(12) United States Patent
Naziruddin et al.

(10) Patent No.: US 8,637,494 B2
(45) Date of Patent: Jan. 28, 2014

(54) METHOD OF ACHIEVING NORMOGLYCEMIA IN DIABETICS BY ADMINISTRATION OF WITHAFERIN A

(75) Inventors: Bashoo Naziruddin, Plano, TX (US); Han Peng, Dallas, TX (US); Shinichi Matsumoto, Arlington, TX (US); Marlon F. Levy, Dallas, TX (US)

(73) Assignee: Baylor Research Institute, Dallas, TX (US)

( * ) Notice: Subject to any disclaimer, the term of this patent is extended or adjusted under 35 U.S.C. 154(b) by 286 days.

(21) Appl. No.: 13/160,334

(22) Filed: Jun. 14, 2011

(65) Prior Publication Data

US 2011/0305719 A1    Dec. 15, 2011

Related U.S. Application Data

(60) Provisional application No. 61/354,497, filed on Jun. 14, 2010.

(51) Int. Cl.
*A01N 45/00*    (2006.01)
*A61K 31/56*    (2006.01)

(52) U.S. Cl.
USPC ........................................ 514/169

(58) Field of Classification Search
None
See application file for complete search history.

(56) References Cited

U.S. PATENT DOCUMENTS 7,695,718 B2    4/2010  Solinger et al.

FOREIGN PATENT DOCUMENTS

WO    2010053655 A2    5/2010

OTHER PUBLICATIONS

Peng H et al. Transplantation Proceedings 42:2058-2061, Jul.-Aug. 2010.*
Baker, Marshall S., et al., "Proinflammatory Cytokines Induce NF-kB-Dependent.NO-Independent Chemokine Gene Expression in MIN6 B Cells," Journal of Surgical Research, (2003), 110:295-303.
Flodstrom, Malin, et al., "Cytokines Activate the Nuclear Factor kB (NF-kB) and Induce Nitric Oxide Production in Human Pancreatic Islets," FEBS Letters, (1996), 385:4-6.
International Search Report and Written Opinion for PCT/US2011/040380, Dated Aug. 31, 2011, 12 pages.
Maitra, Rangan, et al., "Inhibition of NFKB by the Natural Product Withaferin A in Cellular Models of Cystic Fibrosis Inflammation," Journal of Inflamation, (2009), 6:15, 5 pages.
Peng, H., et al., "Inhibition of Inflammatory Cytokine-Induced Response in Human Islet Cells by Withaferin A," Transplantation Proceedings, (2010), 42:2058-2061.
Riachy, Rita, et al., "1,25-Dihydroxyvitamin D3 Protect RINm5F and Human Islet Cells Against Cytokine-Induced Apoptosis: Implication of the Antiapoptotic Protein A20," Endocrinology, (2002), 143(12):4809-4819.

\* cited by examiner

*Primary Examiner* — Robert Landsman
(74) *Attorney, Agent, or Firm* — Fulbright & Jaworski LLP

(57) ABSTRACT

Method and compositions for reducing the inflammation after cytokine exposure of an islet cell transplant without affecting the viability and potency are disclosed herein. The present invention describes a composition comprising Withaferin A (WA), a steroidal lactone derived from *Withania somnifera* to effectively block NF-kB activation in beta cells, minimize cytokine-induced cell death and improve survival of transplanted islets. The method of the present invention involves identifying a subject having islet cells in need of treatment; and providing a effective amount of a Withaferin A composition disposed in a pharmaceutically acceptable carrier in an amount sufficient to reduce the inflammation after cytokine exposure without affecting the viability and potency of the islet cell population.

5 Claims, 20 Drawing Sheets

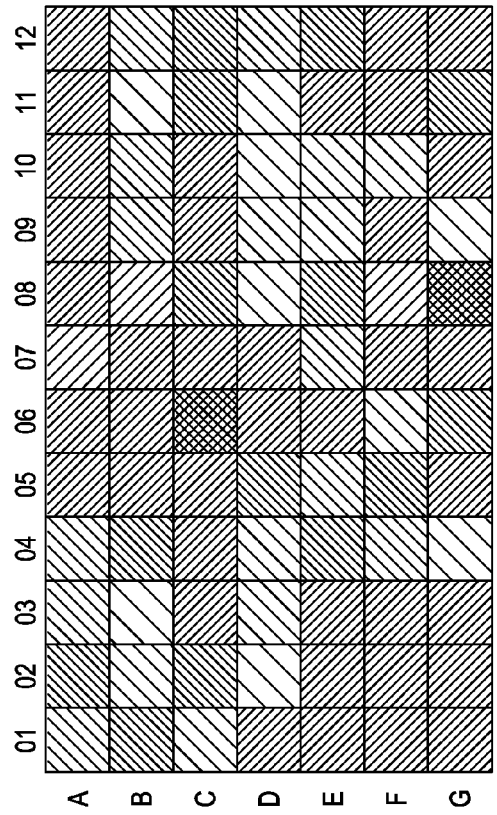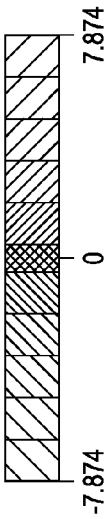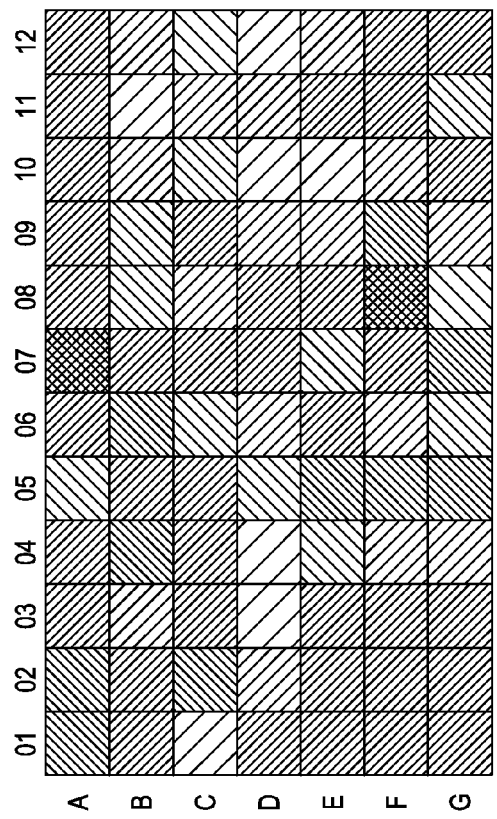
FIG. 1A
FIG. 1B

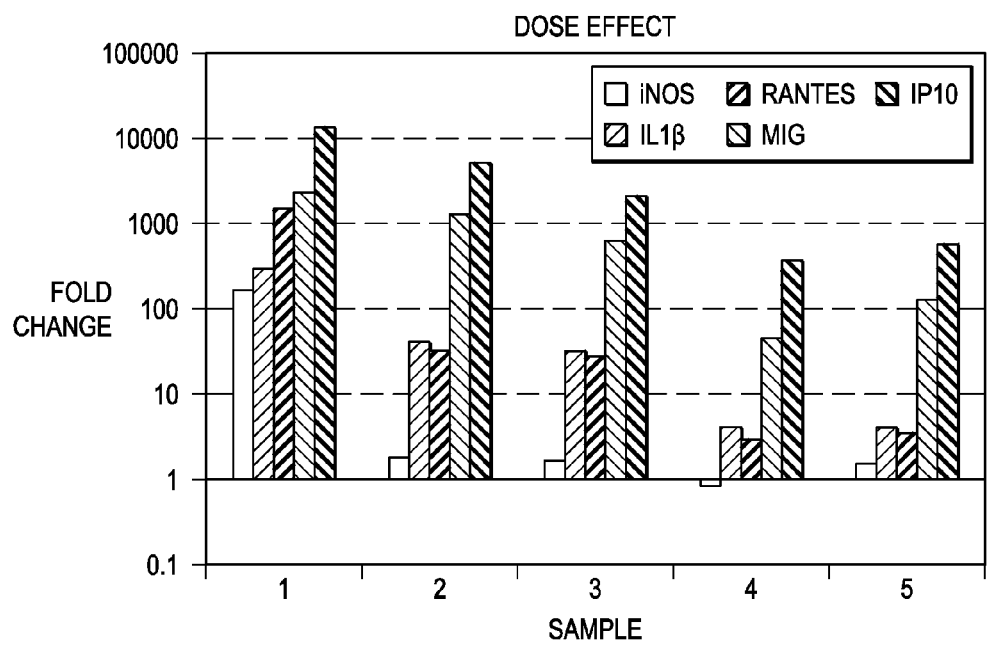
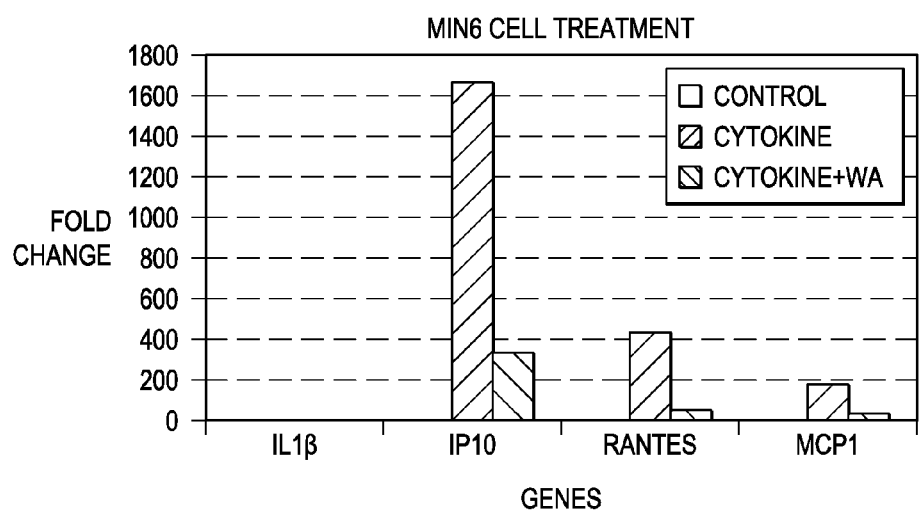

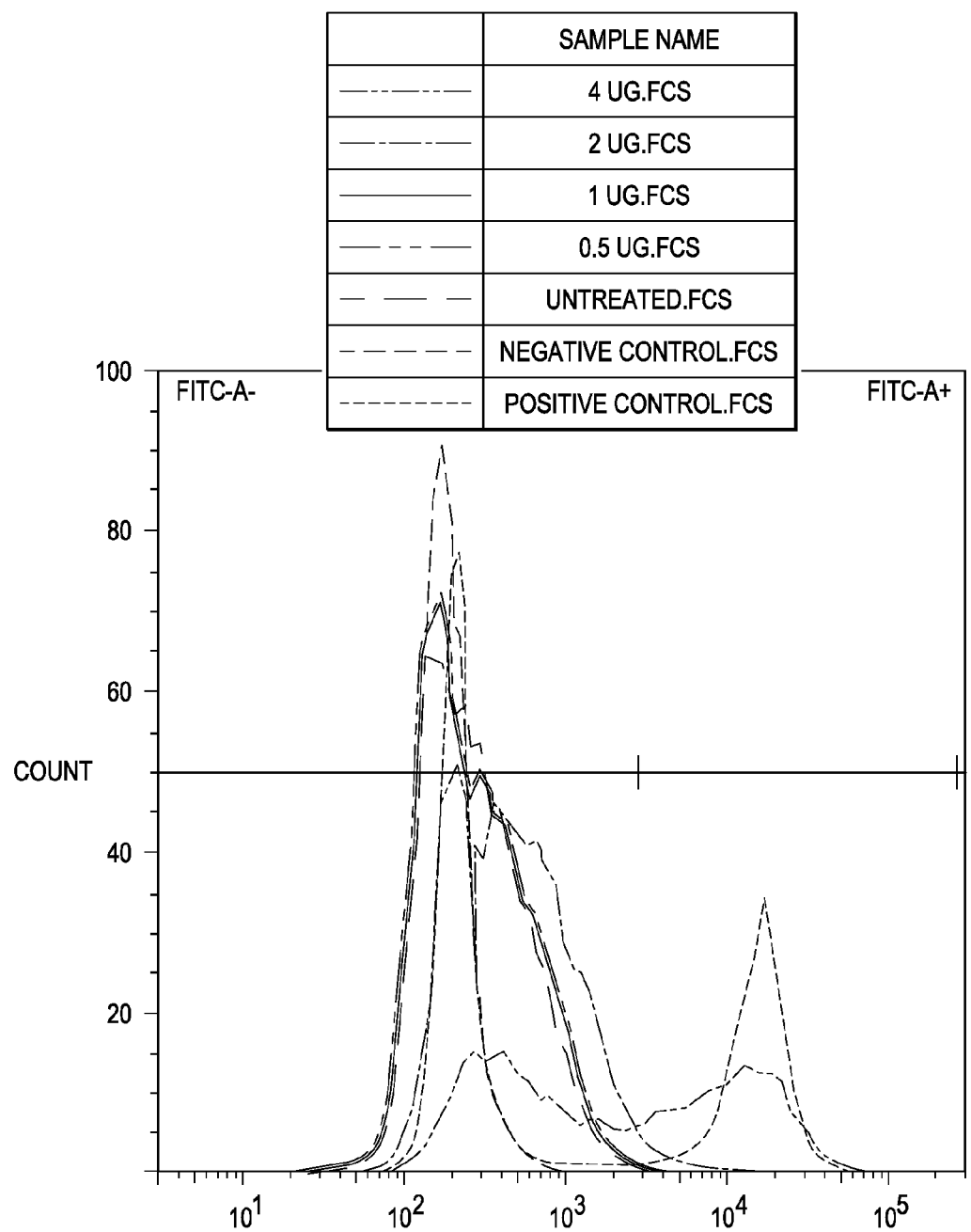

\* p<0.05 for 48h
\*\*p<0.001 for 24h and 48h

* p<0.05

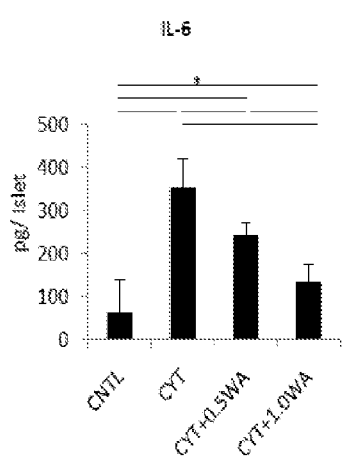 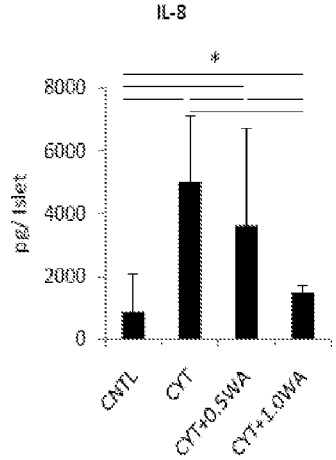 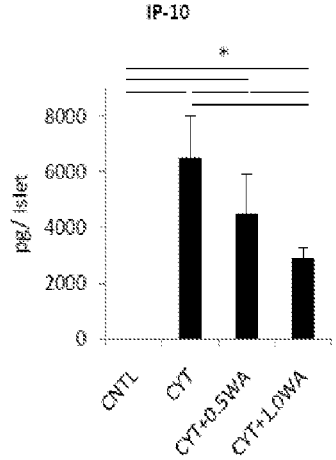
FIG. 8A      FIG. 8B      FIG. 8C
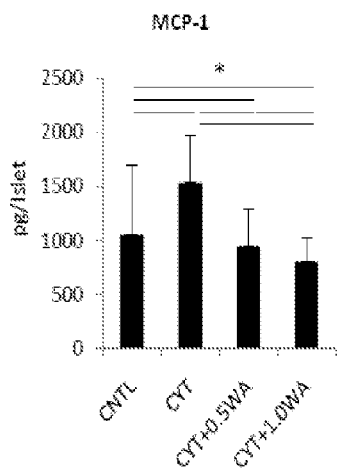 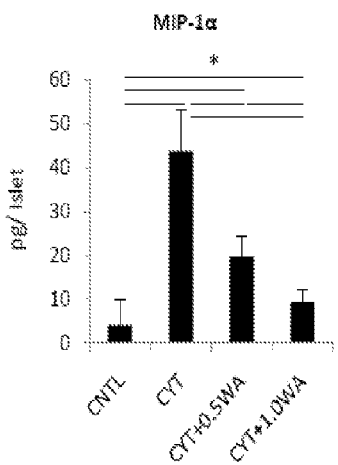 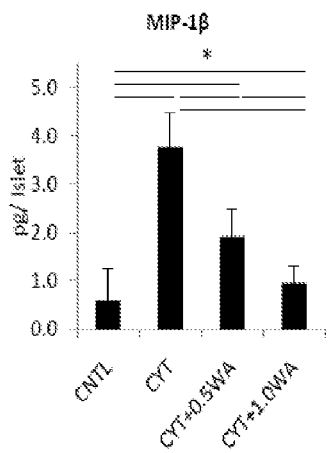
FIG. 8D      FIG. 8E      FIG. 8F

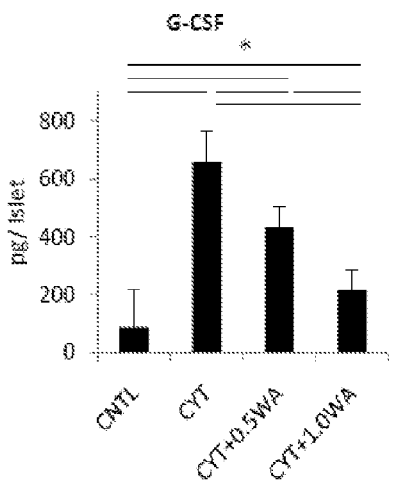
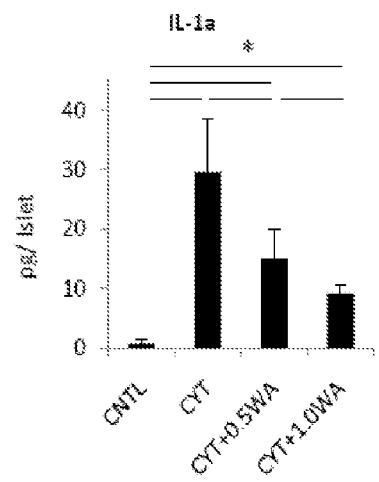
FIG. 8G      FIG. 8H
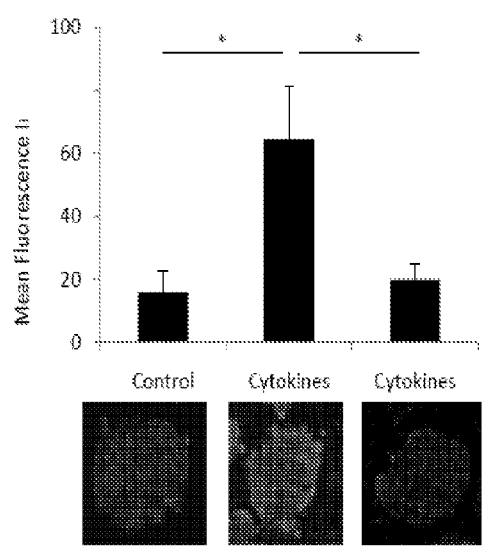
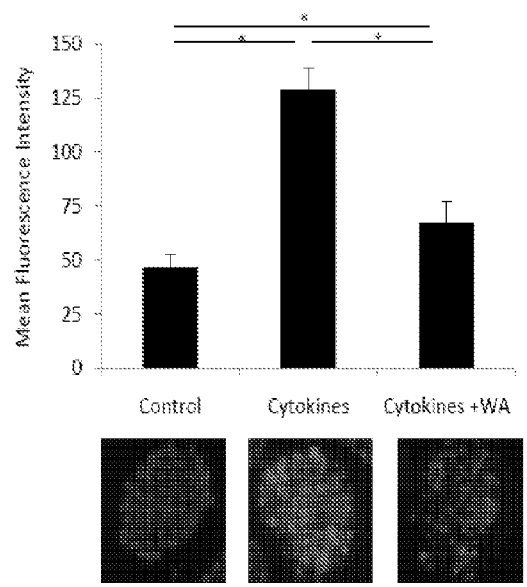
* $p<0.05$
FIG. 9A      FIG. 9B

* p<0.05

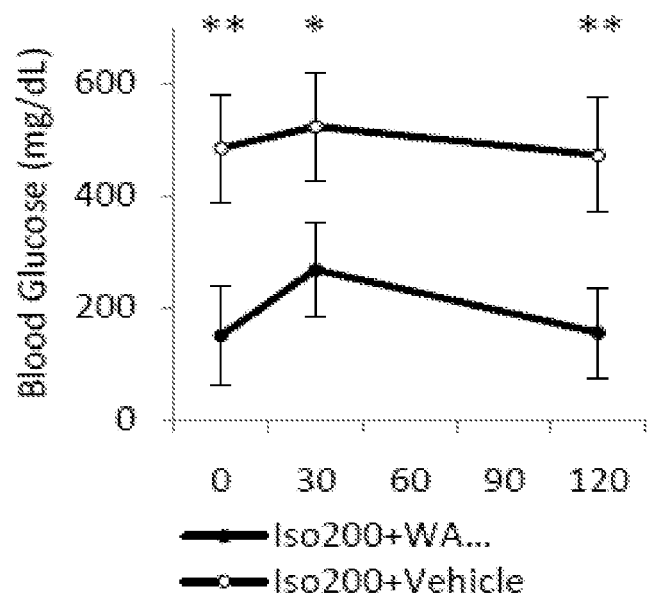
*FIG. 11E*
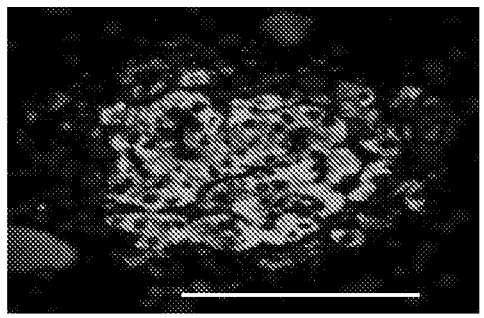
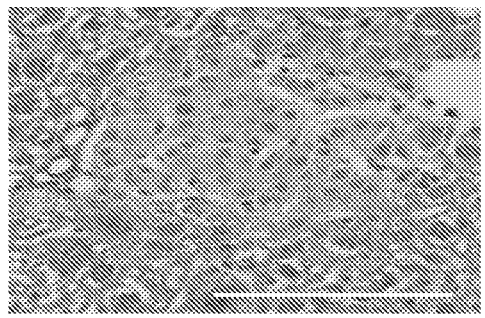
\* p<0.005
\*\*p<0.001
*FIG. 11F*  *FIG. 11G*

METHOD OF ACHIEVING NORMOGLYCEMIA IN DIABETICS BY ADMINISTRATION OF WITHAFERIN A

CROSS-REFERENCE TO RELATED APPLICATIONS

This patent application is a non-provisional application of U.S. provisional patent application 61/354,497 filed on Jun. 14, 2010 and entitled "Inhibition of Pro-Inflammatory Cytokine Induced Response" which is hereby incorporated by reference in its entirety.

TECHNICAL FIELD OF THE INVENTION

The present invention relates in general to the field of inhibition of inflammatory responses, specifically to compositions of matter and methods of making and using Withaferin A for the treatment of pro-inflammatory cytokine induced response of islet cells.

STATEMENT OF FEDERALLY FUNDED RESEARCH

None.

REFERENCE TO A SEQUENCE LISTING

None.

BACKGROUND OF THE INVENTION

Without limiting the scope of the invention, its background is described in connection with cytokine-induced response, pro-inflammatory treatments, methods and compositions to maintain viability and reduce inflammation and apoptosis of transplanted islet cells.

Islet cell transplantation (ICTx) has emerged as a promising alternative therapy for "brittle" Type I diabetes mellitus (T1DM) in recent years and involves isolating the islets from deceased donor pancreas and transplanting them into T1DM patient liver. Successful transplantation can improve glycemic control, relieve the patient from insulin dependence and improve quality of life. However, clinical outcome is not always good due to significant loss of islet mass during or after transplantation. The loss of islets is caused by several reasons including instant blood-mediated inflammatory reaction (IBMIR) and adaptive immune response. There is incremental evidence that cytokines play a crucial role in both processes. Cytokines themselves can directly trigger islet cell death.

U.S. Pat. No. 7,695,718 issued to Scolinger et al. (2010) discloses methods for the treatment and/or prevention of Type 2 diabetes, insulin resistance and disease states and conditions characterized by insulin resistance, obesity, hyperglycemia, hyperinsulinemia and Type 1 diabetes, comprising administering to a subject an effective amount of anti-IL-1 beta antibody or fragment thereof.

U.S. Patent Publication No. 20090093434 (Thompson and Dinarello, 2009) relates to methods for improving the viability, recovery and functionality of islets that are separated from a donor organ for subsequent transplantation and more particularly relates to the use of eIF-5A1 siRNAs to enhance the viability and functionality of islets.

U.S. Patent Publication No. 20110008343 (Lambris et al. 2011) relates to methods for reducing rejection of pancreatic islet cells transplanted into a subject. The methods involve transplanting pancreatic islet cells into a subject in the presence of a complement inhibitor, alone or combined with dextran sulfate.

SUMMARY OF THE INVENTION

In one embodiment, the present invention is a method of reducing inflammation after cytokine exposure without affecting the viability and potency of pancreatic islet cells comprising the steps of: identifying a subject in need of pancreatic islet cells; and providing an effective amount of a Withaferin A composition in an amount sufficient to reduce inflammation of or about the pancreatic islet cells without affecting the viability and the potency of the pancreatic islet cells. In one aspect, the method may further comprise the step of providing a pharmaceutically effective amount of an agent that inhibits transplant rejection. In another aspect, the method may further comprise the step of providing a pharmaceutically effective amount of a tacrolimus composition, a mycophenolic acid or both. In one aspect, the method may include the step of administering the effective amount of the Withaferin A composition is for about 7 days. In one aspect, the method may include the step of administering an effective amount of a Withaferin A is concurrent with a transplant of the pancreatic islet cells. In one aspect, the effective amount of the Withaferin A composition affects the expression one or more inflammatory genes selected from RANTES/CCL5, IP10/CXCL10, MIG/CXCL9, ITAC/CXCL11, TNFα, IL-1β, IL-1α, MCP-2, and CXCL. In one aspect, the Withaferin A is disposed in a pharmaceutically acceptable carrier. In one aspect, the effective amount of the Withaferin A composition is administered by one or more routes of administration selected from the group consisting of oral, intravenous, intraperitoneal, intraportal, subcutaneous, or any combinations thereof.

Yet another embodiment is a pharmaceutical composition for the treatment of an inflammatory response to pancreatic islet cells comprising an effective amount of a Withaferin A composition disposed in a pharmaceutically acceptable carrier adapted for the treatment of a pro-inflammatory cytokine induced response to one or more pancreatic islet cells. In one aspect, the composition may further comprise a pharmaceutically effective amount of a tacrolimus composition, a mycophenolic acid or both. In one aspect, the pharmaceutical composition is provided for 7 days. In another aspect, the effective amount of Withaferin A provided is concurrent with a transplant of the pancreatic islet cells. In another aspect, the effective amount of the Withaferin A composition affects one or more inflammatory genes selected from RANTES/CCL5, IP10/CXCL10, MIG/CXCL9, ITAC/CXCL11, TNFα, IL-1β, IL-1α, MCP-2 and CXCL. In another aspect, the effective amount of the Withaferin A composition is administered orally, intravenously, subcutaneously, intraperitoneally, intraportally, or any combinations thereof. In another aspect, the effective amount of the Withaferin A composition does not affect a potency of the pancreatic islet cells, a viability of the pancreatic islet cells, or both. In another aspect, the amount of the Withaferin A in the Withaferin A composition ranges from 0.25 µg/mL to 1 µg/mL.

Yet another embodiment is a method of reducing inflammatory gene expression caused by the transplantation of one or more pancreatic islets comprising the steps of: identifying a subject in need of reduction of inflammatory gene expression against pancreatic islets; and providing an effective amount of a Withaferin A composition disposed in a pharmaceutically acceptable carrier adapted to reduce the expression of one or more inflammatory genes against the pancreatic islets. In one aspect, the method may further comprise the step of providing a pharmaceutically effective amount of an agent that inhibits transplant rejection. In another aspect, the method may further comprise the step of providing a pharmaceutically effective amount of a tacrolimus composition, a mycophenolic acid or both. In one aspect, the method may include the step of administering the effective amount of the Withaferin A composition is for about 7 days. In one aspect, the method may include the step of administering an effective amount of a Withaferin A is concurrent with a transplant of the pancreatic islets. In one aspect, the effective amount of the Withaferin A composition affects the expression one or more inflammatory genes selected from RANTES/CCL5, IP10/CXCL10, MIG/CXCL9, ITAC/CXCL11, TNFα, IL-1β, IL-1α, MCP-2, and CXCL. In one aspect, the Withaferin A is disposed in a pharmaceutically acceptable carrier. In one aspect, the effective amount of the Withaferin A composition is administered by one or more routes of administration selected from the group consisting of oral, intravenous, intraperitoneal, intraportal, subcutaneous, or any combinations thereof.

Yet another embodiment of the present invention is an immunosuppressive composition comprising one or more immunosuppressive agents selected from the group consisting of daclizumab, sirolimus, tacrolimus, glucocorticoids, cytostatics, and any combinations thereof; Withaferin A; and a pharmaceutically acceptable carrier, wherein the one or more immunosuppressive agents, the Withaferin A, or both are dissolved or dispersed in the carrier in an amount effective to provide immunosuppression, reduce inflammation, or both following islet cell transplantation in a human or animal subject. In one aspect, the Withaferin A affects one or more inflammatory genes selected from the group consisting of RANTES/CCL5, IP10/CXCL10, MIG/CXCL9, ITAC/CXCL11, TNFα, IL-1β, IL-1α, MCP-2, and CXCL. In another aspect, the composition does not affect a potency or a viability of a population of transplanted islet cells.

Yet another embodiment is a method of preventing or reducing rejection, an inflammatory response, or both in a population of transplanted islet cells comprising the steps of: identifying a human subject in need of prevention or reduction of the rejection, the inflammatory response, or both in the population of the transplanted islet cells; and administering a composition to the human subject comprising: one or more immunosuppressive agents selected from the group consisting of daclizumab, sirolimus, tacrolimus, glucocorticoids, cytostatics, and any combinations thereof; Withaferin A; and a pharmaceutically acceptable carrier, wherein the one or more immunosuppressive agents, the Withaferin A, or both are dissolved or dispersed in the carrier in an amount effective to provide immunosuppression, reduce inflammation, or both following islet cell transplantation in the human subject.

Another embodiment of the present invention is a method of reducing number of islet cells to be transplanted, increasing a functional mass of transplanted islet cells, or both in a diabetic human subject to achieve normoglycemia comprising the steps of: providing a sub-optimal dose of islet cells to be transplanted in the human subject; transplanting the sub-optimal dose of the islet cells in the human subject; and treating the islet cells with an effective amount of a Withaferin A composition disposed in a pharmaceutically acceptable carrier. In one aspect, the Withaferin A composition is provided to the subject at one or more intervals for a fixed period of time following transplantation of the sub-optimal dose of the islet cells. In another aspect, the sub-optimal dose is further defined as a dose of islet cells insufficient to produce a normoglycemia in the diabetic subject. In another aspect, the composition reduces an inflammation in the sub-optimal dose of the transplanted islets after cytokine exposure without affecting the viability and the potency of the one or more transplanted islet cells. In one aspect, the Withaferin A composition is combined with the islet cells prior to, or during, transplantation.

BRIEF DESCRIPTION OF THE DRAWINGS

For a more complete understanding of the features and advantages of the present invention, reference is now made to the detailed description of the invention along with the accompanying figures and in which:

FIGS. 1A-1C are plots of the effect of Withaferin A on gene transcription;

FIGS. 2A-2F are bar graphs of gene expressions with Withaferin A concentration;

FIGS. 4A to 4D illustrate the mean channel fluorescence data showed when islets were treated with the cytokine mix; FIG. 4B is plot of a Withaferin A viability test; FIG. 4C is a plot of the dose effect of Withaferin A on apoptosis; FIG. 4D is a plot of the insulin secretion level of Withaferin A and control samples;

FIGS. 8A-8H show that Withaferin A inhibits a multitude of inflammatory cytokines and chemokines Five sets of fifty handpicked, human islets were cultured for 96 hours in cytokines or cytokines supplemented with Withaferin A at 37° C. Supernatant was collected and analyzed in duplicate with Millipore's human cytokine detection kit in the Luminex 200®. Results were standardized to the number of islets. Graphical representations are expressed as means±STD. Significant differences between mean values groups as determined by Turkey-Kramer post-hoc tests are indicated by an asterisk (*p<0.05) above bars;

FIGS. 9A and 9B show that the inflammatory cytokine production originates from islets: Human islets were exposed to the cytokine cocktail with (9B) or without Withaferin A (9B) for 24 hours, then islets were fixed in formalin, embedded in paraffin, sectioned, then underwent heat-mediated antigen retrieval for 20 minutes before being probed for insulin (not shown), MCP-1 (A, top, red), IP-10 (A, bottom, red) and DNA (blue). Islet sections were captured under similar conditions and mean fluorescent intensity values were measured. Intracellular staining revealed significantly higher levels of MCP-1 (B) and IP-10 (C) in islets exposed to cytokines, whereas these levels were decreased by adding 0.5 µg/mL Withaferin A. Graphical representations are expressed as means±STD. Significant differences between mean values groups as determined by Turkey-Kramer post-hoc tests are indicated by an asterisk (*p<0.05) above bars;

FIGS. 11A-11G show that the intraportal islet isograft survival is improved by Withaferin A administration as demonstrated by blood glucose levels, glucose tolerance test, and histological evaluation: Intraportal islet transplantation into C57BL/6 mice has a success rate of 100% (3/3) with 400 islets (11A) from a genetically identical donor, but using a 200 islet isograft with injection of 0.5 mL PBS (vehicle) resulted in 0% (0/5) of recipients achieving normoglycemia (11B). However, daily administration of 25 ug Withaferin A (11C) starting immediately after transplantation and lasting 7 days yielded a much higher success rate of 83% (5/6). Intraperitoneal glucose tolerance test was performed on day 30 post transplant to assess glycemic control of Withaferin A-treated and vehicle-treated (11E) mice; also naïve and STZ-induced diabetic mice were challenged with glucose for comparison. After 12-14 hours of fasting, mice were injected with a 5% glucose solution (1 mg/kg body weight) and blood glucose levels were monitored at 0, 30, and 120 minutes afterwards. There was a significant difference in blood glucose levels at each time. Naïve and Withaferin A treated mice demonstrated a similar pattern with normalization of blood glucose levels below 200 mg/dL after 120 minutes. After thirty days, hepatectomy of recipient mice was performed and the liver was fixed in formalin, embedded in paraffin and stained for insulin (11F) and H&E (11G). This demonstrated functional islets engrafted into the hepatic venules.

DETAILED DESCRIPTION OF THE INVENTION

Figure 1C:
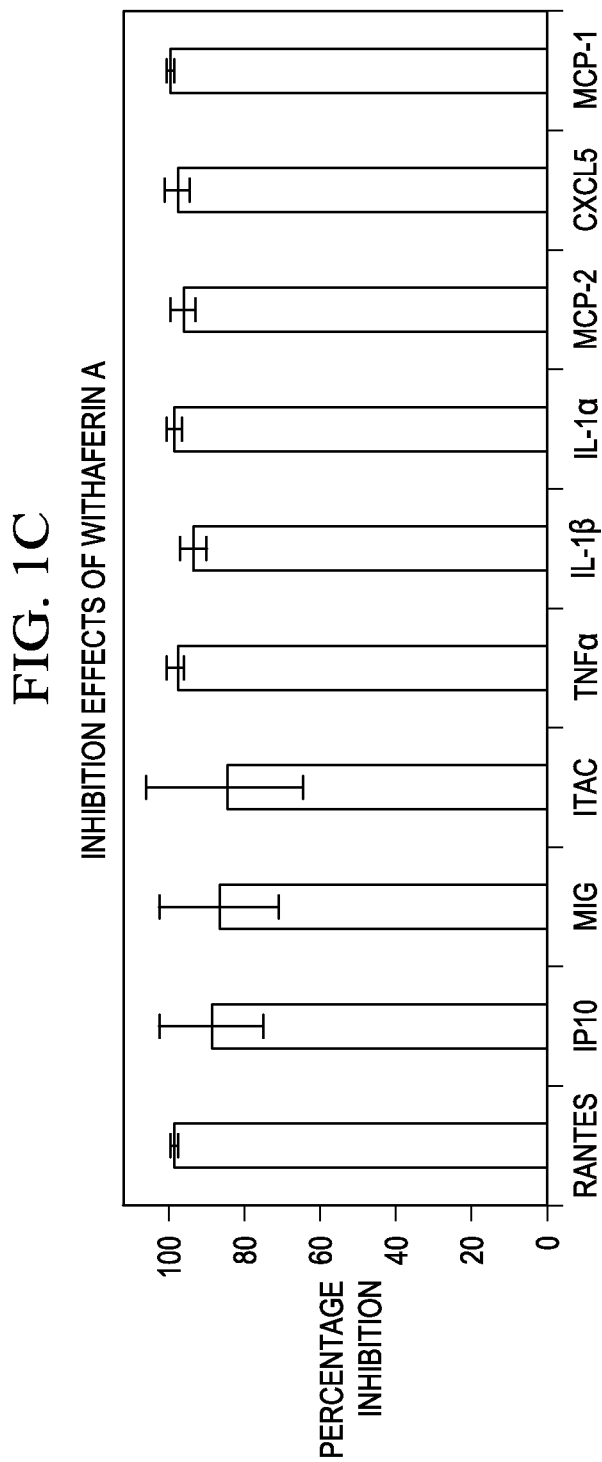

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The term "diabetes" as described in embodiments of the present invention refers to the chronic disease characterized by relative or absolute deficiency of insulin that results in glucose intolerance. The term "diabetes" is also intended to include those individuals with hyperglycemia, including chronic hyperglycemia, hyperinsulinemia, impaired glucose homeostasis or tolerance, and insulin resistance.

The term "insulin" as used herein shall be interpreted to encompass insulin analogs, natural extracted human insulin, recombinantly produced human insulin, insulin extracted from bovine and/or porcine sources, recombinantly produced porcine and bovine insulin and mixtures of any of these insulin products. The term is intended to encompass the polypeptide normally used in the treatment of diabetics in a substantially purified form but encompasses the use of the term in its commercially available pharmaceutical form, which includes additional excipients. The insulin is preferably recombinantly produced and may be dehydrated (completely dried) or in solution.

The term "islet cell (s)" as used throughout the specification is a general term to describe the clumps of cells within the pancreas known as islets, e.g., islets of Langerhans. Islets of Langerhans contain several cell types that include, e.g., β-cells (which make insulin), α-cells (which produce glucagons), γ-cells (which make somatostatin), F cells (which produce pancreatic polypeptide), enterochromaffin cells (which produce serotonin), PP cells and D1 cells.

The term "population of cells" according to the present invention refers to a population of individual cells, as well as cells in tissues and organs or parts thereof; or cells obtained from whole organisms. As regards to pancreatic islet cells the skilled artisan will understand that these include those cells generally found in close association with the beta cells found in the Islets of Langerhans region of the pancreas. When isolating the islets for transplantation or for other purposes, it is common for the "population of cells" to include more than just beta cells, i.e., it may also comprise alpha cells, delta cells, pancreatic polypeptide (PP) producing cells, and epsilon cells.

The term "gene" is used to refer to a functional protein, polypeptide or peptide-encoding unit. As will be understood by those in the art, this functional term includes both genomic sequences, cDNA sequences, or fragments or combinations thereof, as well as gene products, including those that may have been altered by the hand of man. Purified genes, nucleic acids, protein and the like are used to refer to these entities when identified and separated from at least one contaminating nucleic acid or protein with which it is ordinarily associated The term "inflammation" in the broadest sense refers to all the processes developed by living organisms in response to an aggression of internal or external origin.

The term "cytokine" as used herein refers to any secreted polypeptide that affects the functions of other cells, and is a molecule which modulates interactions between cells in the immune or inflammatory response. A cytokine includes, but is not limited to monokines and lymphokines regardless of which cells produce them. For instance, a monokine is generally referred to as being produced and secreted by a mononuclear cell, such as a macrophage and/or monocyte but many other cells produce monokines, such as natural killer cells, fibroblasts, basophils, neutrophils, endothelial cells, brain astrocytes, bone marrow stromal cells, epideral keratinocytes, and β-lymphocytes. Lymphokines are generally referred to as being produced by lymphocyte cells. Examples of cytokines include, but are not limited to, interleukin-1 (IL-1), tumor necrosis factor-alpha (TNFα) and tumor necrosis factor beta (TNFβ).

As used herein, the term "in vivo" refers to being inside the body. The term "in vitro" used as used in the present application is to be understood as indicating an operation carried out in a non-living system.

The terms "administration of" or "administering a" as used herein refers to providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as intravenous (IV), intramuscular (IM), or intraperitoneal (IP), and the like; transdermal dosage forms, including creams, jellies, powders, or patches; buccal dosage forms; inhalation powders, sprays, suspensions, and the like, and rectal suppositories.

In general, compounds of this invention can be administered as pharmaceutical compositions by any one of the following routes: oral, systemic (e.g., transdermal, intranasal or by suppository), or parenteral (e.g., intramuscular, intravenous or subcutaneous) administration. One manner of administration is oral using a convenient daily dosage regimen which can be adjusted according to the degree of affliction. Compositions can take the form of tablets, pills, capsules, semisolids, powders, sustained release formulations, solutions, suspensions, elixirs, aerosols, or any other appropriate compositions. Another manner for administering compounds of this invention is inhalation.

The terms "effective amount" or "therapeutically effective amount" refers to the amount of the subject compound that will elicit the biological or medical response of a tissue, system, animal or human that is being sought by the researcher, veterinarian, medical doctor or other clinician As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology).

The present invention describes compositions and methods to protect against pro-inflammatory cytokine induced cell damage and to improve survival of transplanted islets. The present invention describes Withaferin A (WA), a steroidal lactone derived from *Withania somnifera* to effectively block NF-kB activation in beta cells, minimize cytokine-induced cell death and improve survival of transplanted islets. The Withaferin A described herein can be incorporated as adjunct to immunosuppressive regimen to improve islet transplant outcome.

Type 1 diabetes mellitus (T1D) is an autoimmune disorder than leads to destruction of the insulin producing beta cells of the pancreas. Islet cell transplantation to replace depleted beta cells has emerged as an effective treatment in recent years. However, a substantial number of islets are destroyed by the immediate blood mediated immune response (IBMIR).[1] This blood mediated nonspecific immune response is characterized by coagulation, complement activation, platelet aggregation, and cytokine storm.[2] Cytokines such as TNF-α, IFN-γ, and IL-1β have important pro-inflammatory and pro-apoptotic roles in T1D and islet transplantation.[3,4,5] Although immunosuppressants are administered after transplantation of islets, they do not target cytokine mediated damage to islets.

Inflammatory reaction is one of the major reasons for islet cell loss immediately after islet cell transplantation. Inflammatory cytokines cause beta cell damage through a signal transduction pathway initiated at TNF and IL-1 receptors and mediated through a downstream factor, NF-κB. It has been shown that a cytokine cocktail of TNF-α, IFN-γ, and IL-1β led to NF-κB activation in human islets.[6] Increased pro-inflammatory cytokines at local transplantation site can induce direct islet cell death and promote the secretion of chemokines from islet cells (MCP-1, IP-10, RANTES etc.) to recruit immune cells. However the NF-κB transcription factor regulated in a complex manner and is capable of regulating inflammatory, apoptotic, or survival pathways. Pro-inflammatory cytokines have been shown to induce apoptosis in beta cells.[7] Apoptosis-related proteins can deteriorate islet viability and chemokines can attract immune cells to the transplantation sites. Both lead to islet cell loss. Many anti-inflammatory agents and immunosuppressants have been tested to reduce the inflammatory status of islets. But the inferior outcome could still not be completely reversed. One study examined the dual role of hypoxia and cytokines on NF-κB activation, and proposed that NF-κB activation by cytokines was modulated by different levels of hypoxia.[8] Pro-inflammatory cytokines have also been shown to upregulate several chemokine genes in islets. These chemokines act as chemoattractants for lymphocytes, directing them towards the site of transplantation. This has been observed with CCL2 secretion, demonstrating macrophage infiltration islet grafts leading to a negative clinical outcome.[9] Since NF-κB is a cytokine induced mediator of several apoptotic and inflammatory genes in β-cells, it provides an attractive therapeutic target for inhibition. The present invention provides an anti-inflammatory agent, e.g., Withaferin A (WA), that inhibits the inflammatory response of islet cells.

Withaferin A is a potent inhibitor of NF-κB. The origin of Withaferin A is from a plant species called *Withania som-*

*nifera*, which has been used for centuries in traditional eastern medicine in Middle Eastern countries such as India and Palestine.[10] There are several extracts from the leaves of *Withania somnifera*, but a study by Kaileh et al. identified the steroidal lactone, Withaferin A, as the most potent inhibitor of NF-κB by IκB kinase β hyperphosphorylation preventing IκB degradation.[11] Phsophorylation of the inhibitory protein IκB and its subsequent degradation lead to NF-κB activation and translocation to the nucleus. Withaferin A has been studied as an anti-inflammatory in cystic fibrosis, monosodium urate crystal-induced inflammation, and as an anti-carcinogenic agent[12,13] with further potential to treat rheumatoid arthritis, asthma, inflammatory bowel disease[14], AIDS,[15] and cardiovascular disease.[16]

The present invention demonstrates the clinical relevance of Withaferin A in islet transplantation and studies its effects in preventing cytokine induced damage and islet mediated inflammation. The present inventors have previously demonstrated that inflammatory cytokines cause dramatically increased levels of several inflammatory cytokines and chemokines (iNOS, IL-1β, RANTES, MIG, and IP-10) in human islets as determined by qPCR analysis.[17] However, Withaferin A was able to decrease the mRNA levels of several of these chemokines by ten-fold or more.

Withaferin A used herein was purchased from Enzo Life Sciences (10 mg, purity>99% by HPLC, Plymouth Meeting, Pa.). The Withaferin A was dissolved with sterile DMSO (ATCC, Manassas, Va.) and was diluted into sterile DPBS (Gibco, Carlsbad, Calif.) for a final concentration of 1 mg/mL; this stock solution could be stored at −20° C. for 3 months. The recombinant human cytokines TNF-α (specific activity: $1.1 \times 10^5$ U/μg), IFN-γ (specific activity: $2.0 \times 10^4$ U/μg), and IL-1β (specific activity: $2.0 \times 10^5$ U/μg) were purchased from R&D Systems (Minneapolis, Minn.). The recombinant mouse cytokines TNF-α (specific activity: $2.7 \times 10^5$ U/μg), IFN-γ (specific activity: $8.43 \times 10^3$ U/μg), and IL-1β (specific activity: $1.1 \times 10^6$ U/μg) were also purchased from R&D Systems. Antibodies for NF-κB (GenScript, Piscataway, N.J.), MCP-1 (R&D Systems), IP-10 (AbCam, Cambridge, Mass.), insulin (Sigma-Aldrich, St. Louis, Mo.), were used as primary antibodies while Alexa Fluor® 488 anti-guinea pig (Invitrogen, Carlsbad, Calif.), Alexa Fluor® 594 anti-guinea pig (Invitrogen), Alexa Fluor® 488 goat anti-rabbit (Invitrogen), NorthernLights™ 557 anti-mouse (R&D Systems) were used a secondary fluorescently conjugated antibodies for immunohistochemistry. Antibody diluent, background reducing (DAKO, Carpinteria, Calif.), AquaBlock™/EIA/WB (EastCoast Bio, North Berwick, Me.), and Antigen Retrieval Reagent-Universal (R&D Systems) were also used for immunohistochemistry.

Human Islet Isolation: Human research grade pancreata were obtained through two local organ procurement agencies (LifeGift, Fort Worth, Tex. and Southwest Transplant Alliance, Dallas, Tex.). Pancreatic ductal preservation was performed with I-Kyoto and CSPS solution, and the two-layer method was used for preservation of the organ before isolation. Islet isolation was performed using the modified Ricordi method. Liberase MTF (Roche Diagnostics GmbH, Penzber, Germany) was used as the collagenase to release islets during digestion at 37° C. Islets were purified using an iodixanol based continuous density gradient centrifugation in a COBE 2991 cell processor. Islet yield and purity was assessed with dithizone staining (Sigma Chemical Co., St. Louis, Mo.) (2 mg/mL). Viability was assessed using fluorescein diacetate (FDA) and propidium iodide (PI). Islets used for the studies were 80 to 90% viable, with a purity of 60 to 85%. Human islets used were handpicked to greater than 95% purity. Islets were cultured with CMRL-based human islet culture media containing 0.1% BSA with Kanamycin at 37° C.

Mouse Isolation: Islets were isolated from male inbred B6 (MIN6) mice (C57BL/6N Inbred Mice, Harlan Labs). Collagenase type V (Sigma, C9263) (2 mg/mL) was injected through the common bile duct into the pancreas. Mouse pancreata were digested by incubation at 37° C. for 28 minutes. After washing, the islets were purified with a discontinuous Ficoll based gradient (1.085 g/mL, 1.077 g/mL, and Cap of DMEM) and centrifugation at 1000 rpm for 10 minutes. Purified islets were further purified in a 65 mm dish in DMEM by removing acinar cells to a purity of greater than 95%. Islets were cultured in DMEM supplemented with Kanamycin and 0.1% BSA, mouse islet culture media.

Cytokine & Withaferin A Treatment: After isolation and overnight culture, islets were subjected to an in-vitro model of inflammatory conditions with a cytokine cocktail of the species specific recombinant proteins (1,000 U/mL TNF-α, 1,000 U/mL IFN-γ, and 50 U/mL IL-1β dissolved in human or mouse islet culture media). Islets were treated by Withaferin A co-culture at concentrations ranging from 0.25 to 2.0 μg/mL. Control islets were cultured in the appropriate culture media lacking both the cytokine cocktail and Withaferin A. All islets were cultured in a humidified incubation chamber at 37° C. with 5% $CO_2$ for the indicated time.

Western Blotting: Cells were treated with cytokines for 20 min, then harvested in lysis buffer containing 50 mM HEPES, pH 7.5, 150 mM NaCl, 1% Triton X-100, 0.2 mg/mL phenylmethylsulfonyl fluoride (PMSF), 0.1 M NaF, 2 mM $Na_3VO_4$, 10 μg/mL aprotinin, 5 μg/mL pepstatin A, and 5 μg/mL leupeptin. Proteins were subjected to SDS/polyacrylamide gel electrophoresis and electrotransferred to nitrocellulose membranes. Membranes were blocked with 5% milk in Tris-buffered saline containing 0.1% Tween-20 (TBST) pH 7.4 for 2 hours, incubated with primary antibody for 1 hour at 4° C., and washed three times with TBST. Primary antibodies were IkB-α (C-21) (Santa Cruz) and ERK1/2 as described.[21] Membranes were then incubated with secondary antibodies conjugated to DyLight 680 and 800 fluorescent dyes (Cell Signaling) to detect proteins using an ODYSSEY Infrared Imaging System (LI-COR).

RT-PCR Inflammation Array and Primer Assays: After proper time of treatment, islets were harvested and lysed in lysis buffer (Stratagene, La Jolla Calif.). RNA was purified by Absolutely RNA Miniprep kit (Stratagene) and then reverse transcribed into cDNA by RT2 Firststrand kit (SABiosciences, Frederick Md.). Template cDNA were mixed with RT2 SYBR green/ROX PCR master mix (SABiosciences) and then added to each well of a human inflammation gene array plate (SAbiosciences). The RT-PCR reaction was run in Stratagene MX3000 with following program: 95° C., 10 minutes; 40 cycles of (95° C., 15 second; and 60° C., 60 second). Cycle threshold data was uploaded to a Web-Based PCR Array Data Analysis on SABiosciences website and fold change compared to control was analyzed.

$$\text{Fold change} = 2^{[\Delta Ct(control) - \Delta Ct(Experiment)]}, \Delta Ct = Ct(GOI) - Ct(HKG)$$

Procedure for single gene primer assays was the same except primers of particular genes other than the whole array plate were used.

Immunohistochemical Staining: After culture, islets were embedded in OCT compound, flash frozen in liquid nitrogen and stored at −80° C. until sectioning. Nine μm sections of embedded islets were taken and stained for IP-10 (1:100), MCP-1 (1:20), or insulin (1:75) using standard immunohistochemical techniques. Staining was visualized using an HRP-conjugated secondary antibody conjugated with diaminobenzidine (DAB). Samples were then counterstained with hematoxylin, dehydrated and mounted. Images were acquired.

Immunohistochemistry: Engrafted livers and cytokine treated islets were preserved in 10% formalin, embedded in paraffin and sectioned at 5 µm. Tissue sections were deparaffinized in xylene (twice for 5 minutes) and series of ethanol gradients (100%, 95%, 90%, 80%, 70%, and 50% ethanol diluted with water for 2 minutes each). Next, sections were heated at 98° C. in 1× Antigen Retrieval Reagent-Universal (R&D Systems) for 20 minutes. Then tissue samples were blocked for non-specific bonding by AquaBlock (EastCoast Bio) for 1 hour at room temperature. Next the primary antibody, diluted in a background reducing antibody diluent, was applied overnight at 4° C. Next, the appropriate fluorescently conjugated secondary antibody (diluted 1000×) was applied for 1 hour at room temperature protected from light. Next, the anti-insulin primary antibody was applied (diluted ×500) for 1 hour at room temperature, and subsequently the fluorescently labeled secondary antibody (diluted ×1,000) was incubated with the tissue sample for 1 hour at room temperature. Lastly, a DAPI (0.5 µg/mL) nuclear counterstain was applied for 10 minutes at room temperature before mounting the sample with VectaShield and imaging via fluorescent microscopy (BX16, Olympus DP-72). Micrographs of the fluorescent antibody associated with IP10 or MCP-1 were captured at the same exposure time to ensure fluorescent intensity levels that could be compared among the different experimental conditions. Micrographs were imported to Image J, converted to 8-bit grayscale photos, then the mean fluorescence intensity was measured by limiting the region of interest to a single islet via the thresholding function of the program. Mean fluorescent intensity is calculated at the integrated density divided by the area in the region of interest.

Viability Determination by Hoechst 342/PI: For immediate in vitro determination of necrosis, islets were incubated with Hoechst 342 (10 µg/mL) and propidium iodide (20 µg/mL) for 10 minutes at 37° C. before imaging via fluorescent microscopy. Fluorescent microsgraphs were merged in Image J (NIH Bethesda, Md.) and the propidium iodide positive area was divided by the Hoechst 342 positive area to provide a calculation of islet viability.

TUNEL Assay: The TUNEL assay was performed with ApopTag® fluorescein in situ apoptosis detection kit. After deparaffinization of samples, antigen retrieval was performed with proteinase K and insulin staining was performed as described previously. Next, digoxigenin labeled nucleotides were added to DNA fragments by the enzyme terminal deoxynucelotidyl transferase (TdT) by incubation at 37° C. for 1 hour. Fluorescein labeled anti-digoxigenin antibodies are bound to the digoxigenin by incubation at room temperature for 30 minutes. Lastly DAPI is stained as described above, and slides are mounted with VecataShield and visualized with fluorescent microscopy. Apoptotic cells are counted as those that appear fluorescently green in the nuclei of insulin positive cells. All nuclei of insulin positive cells were counted and percentage of TUNEL+ cells was calculated as number of TUNEL positive nuclei divided by the total number of insulin positive beta cells. At least 300 nuclei were counted for each condition.

p65 Translocation Assay: NF-κB, p65, translocation was determined by overlap of Alexa-488 labeled NF-κB and DAPI stained nuclei, pseudocolored red by Image J for visualization. The resulting merged image showed p65 translocation by a yellow colored nuclei resulting from the overlap of the red and green colors. Nuclei positive for activated NF-κB translocation was counted in insulin positive cells and divided by the total number of beta-cells.

Measurement of Secreted Inflammatory Cytokines and Chemokines: Fifty human islets were cultured in human islet culture media for 96 hours with the cytokine and Withaferin A treatment. Secretion of proinflammatory cytokines was determined by measuring cell culture supernatant in a Luminex 200 with a human inflammatory cytokine MagPlex kit (Millipore, Billerica, Mass.). The bead assay was performed according to the manufacturer's instructions with samples in duplicate.

Flow Cytometry. Immediately after treatment, islets were dispersed into single cells by accutase (Innovative Cell Technologies) and fixed/permeablized by BD Cytofix/Cytoperm Plus kit. PE conjugated anti-IP-10 antibodies were used for intracellular staining of the corresponding protein. The expression of IP-10 was measured by PE signal strength using a FACS Canto II flow cytometry machine. Collected data was analyzed by Flowjo.

Glucose Stimulated Static Incubation Assay: Islets in each experimental condition were incubated with low (2.8 mM) and then high (20.0 mM) concentrations of glucose solution in Functionality/Viability Medium CMRL1066 (Mediatech, Inc. Manassas, Va.) for 1 hour each at 37° C. Insulin concentrations were measured by an insulin ELISA kit (ALPCO Diagnostics, Salem, N.H.). The insulin secretion levels were normalized by total DNA of the stimulated islets. Studies were performed in triplicate with 10 islets in each group.

In-vivo Intraportal Transplant: Diabetes was induced in by injecting streptozomycin (STZ 180 mg/kg, 9 mg/mL dissolved in DPBS) into the tail vein. Accu-Chek Aviva® (Roche Diagnostics, Indianapolis, Ind.) was used to monitor blood glucose from the tail vein, and mice were considered diabetic, when their blood glucose was measured as greater than 350 dg/mL for two days in a row. Mice were anesthetized with avertin (20 mg/mL, 0.5 mL/mouse), then two hundred islets were injected into the portal vein by puncturing the portal vein through the pancreas with a 27 gauge, hypodermic needle attached to a glass syringe. The peritoneum was first closed with 5-0 black silk sutures, and before sealing this closure, Withaferin A (25 ug, 0.5 mL/mouse) or vehicle (DPBS) was injected into the peritoneal space. Lastly the skin was closed with a continuous suture, and mice were left to recover under heat lamps until mice became active.

IPGTT: Naïve, transplanted, and STZ induced diabetic mice were used to perform an intraperitoneal glucose tolerance test. The mouse's food was removed for 12-14 hours, then an injection of glucose (1 mg/kg body weight, 5% glucose solution in DPBS) was administered intraperitoneally. Blood glucose was monitored with Accu-Chek at 0, 30, and 120 minutes after the injection.

Statistics: The statistical significance of the assays performed was analyzed by the Student's t-test, two-tailed. ANOVA with Turkey-Kramer post-hoc test was performed on Statview 5.0 (SAS Institute Inc, Cary, N.C.). A significant difference was achieved when p values were lower than 0.05.

Increase in inflammatory gene expression by cytokine treatment can be inhibited by Withaferin A. Human islets were treated with culture medium (control), a cytokine cocktail, and a Withaferin A co-culture and tested for inflammatory gene expression.

Among the 84 examined genes, 4 genes (RANTES/CCL5, IP10/CXCL10, MIG/CXCL9 and ITAC/CXCL11) were upregulated more than 100 fold, 5 genes (TNFα, IL-1β, IL-1α, MCP-2 and CXCL5) were upregulated more than 10 fold in the cytokine treated group when compared to control group in all 3 donors. (FIG. 1A). FIGS. 1A, 1B, and 1C are plots of the effect of Withaferin A on gene transcription, with FIG. 1C being a plot of the inhibition effect of Withaferin A on various genes. There was no significant difference between Withaferin A treated group and control (data not shown). However, when cytokine and Withaferin A treated group were compared to cytokine alone treated group, almost all the genes mentioned above were significantly down regulated which indicated a strong anti-inflammatory effect of Withaferin A as seen in the plot of FIG. 1B. Gene MCP-1/CCL2 has been reported to be crucial for islet survival was also included. In all three donors, a 60%-100% inhibition is observed as indicated in the plot of FIG. 1C.

Withaferin A can effectively inhibit inflammatory gene expression at all the time points examined in a dose dependent manner. The optimal dose for the inhibitory effect of Withaferin A in cell culture was determined. 4 critical genes from the inflammation array were selected as representative genes: RANTES, IP10, MIG, IL-1β and an apoptosis related gene iNOS as markers but the skilled artisan will readily note that other genes may be used. Withaferin A at concentrations of 0.5 μg, 1 μg, 2 μg and 4 μg per mL was tested in islet cell culture with same cytokine concentration as previously mentioned.

Figure 2C:
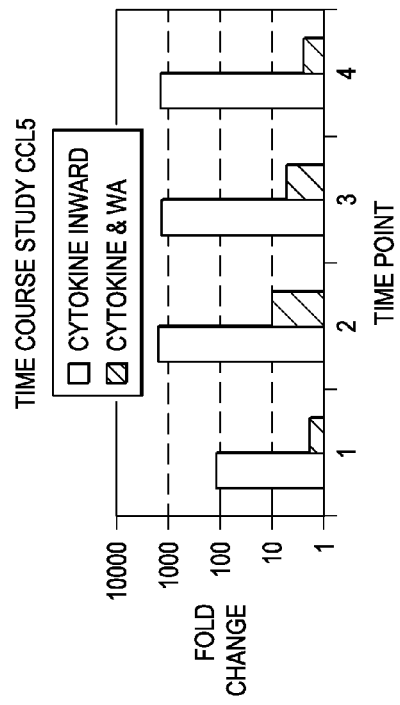
Figure 2D:
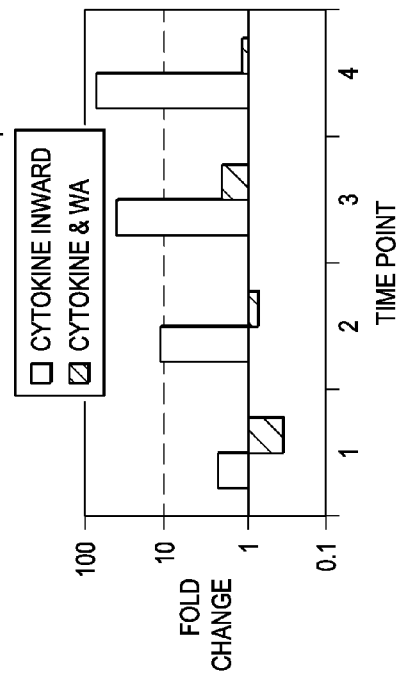
Figure 2E:
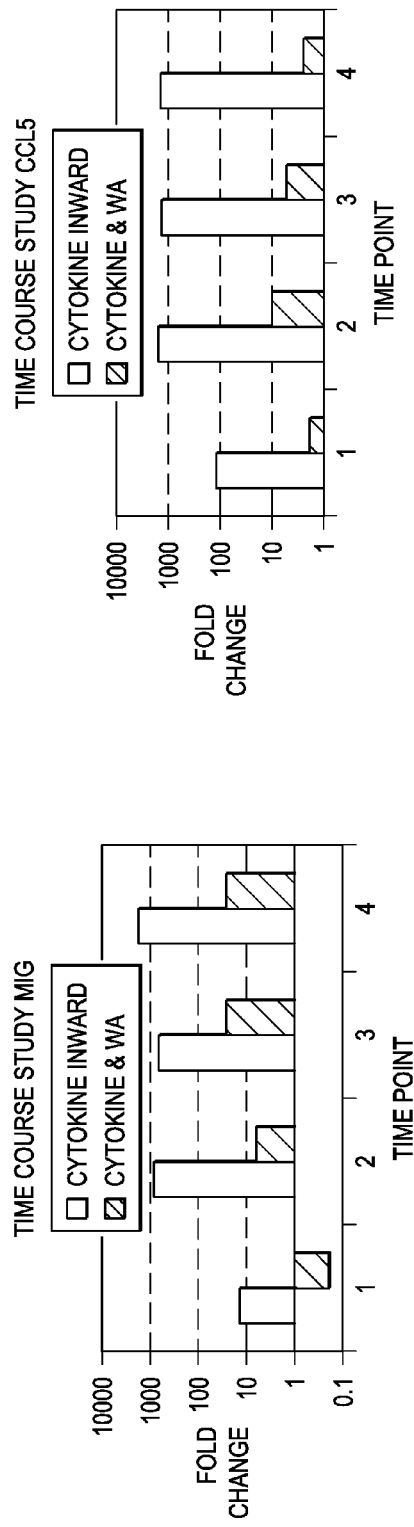
Figure 2F:
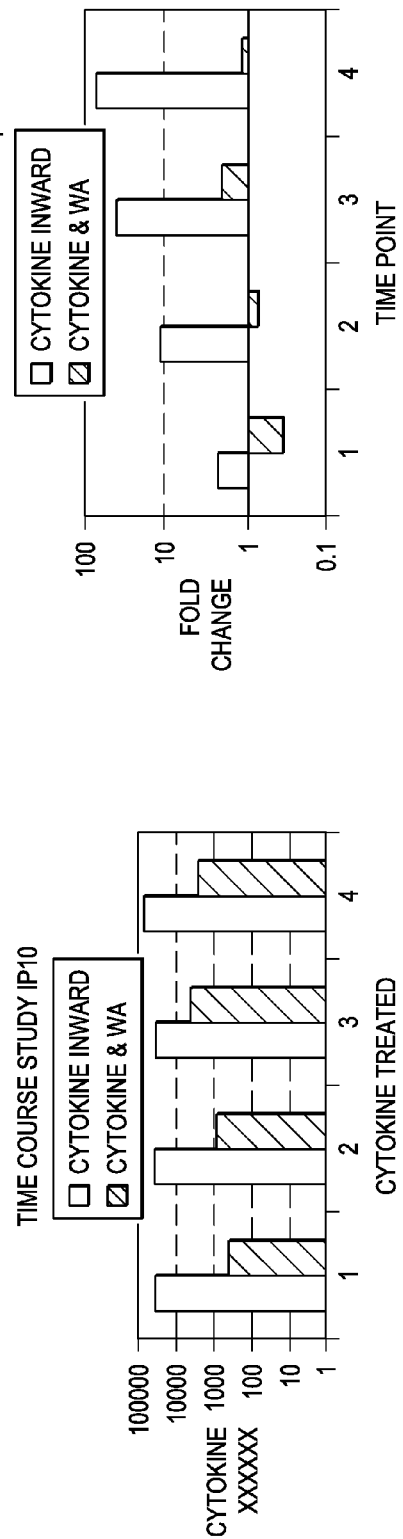

FIGS. 2A-2F are bar graphs of gene expressions with Withaferin A concentration. As shown in FIG. 2A, all expressions of all the 5 genes were decreased with the increase in Withaferin A concentration. The anti-inflammatory effect of Withaferin A at various time points was also evaluated. Islet cells treated with 1 μg Withaferin A and cytokines were harvested at 12 hour, 24 hour, 36 hour, and 48 hour. Expression level of IL-1β, RANTES, MIG and IP-10 were examined. In all time points examined, the expression levels of these four genes were significantly inhibited by Withaferin A when compared to cytokine alone group as shown in logarithmic scale bar (FIGS. 2C-2F). The inhibitory effects of Withaferin A on MIN6, a mouse beta cell line was also evaluated (FIG. 2B). IP10, RANTES and MCP-1 were highly upregulated upon cytokine treatment and could be inhibited by Withaferin A. However, unlike human islets IL1beta was not up-regulated.

Figure 3A:
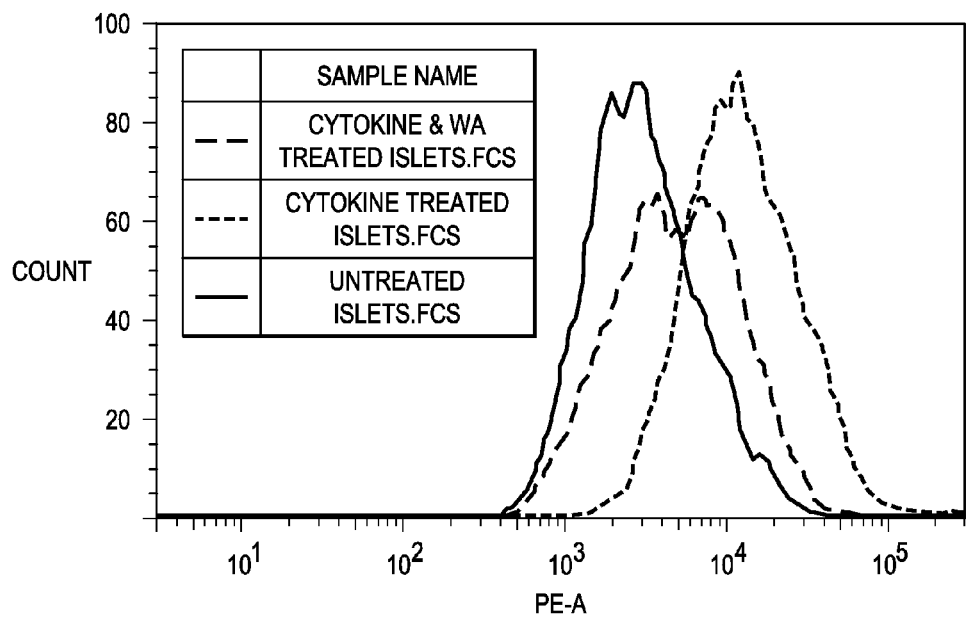
FIGS. 3A-3C show the detection of the inhibitory effects of Withaferin A at protein level.
Figure 3B:
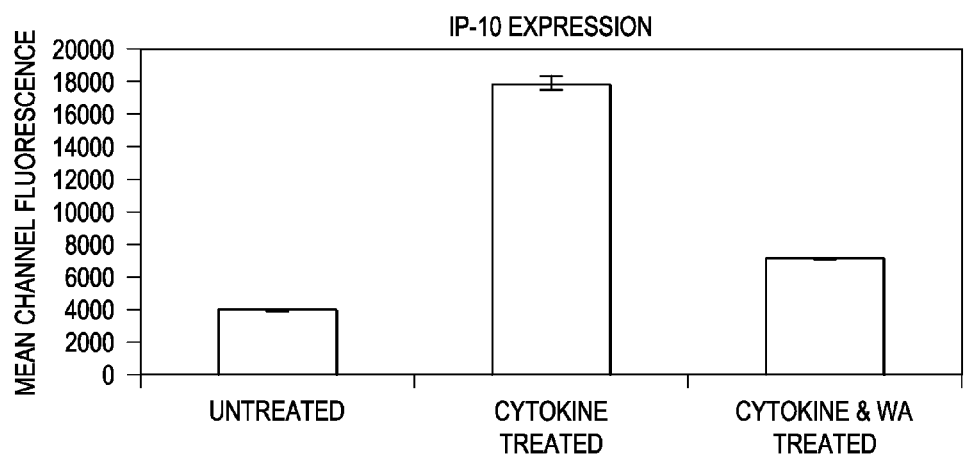
Figure 3C:
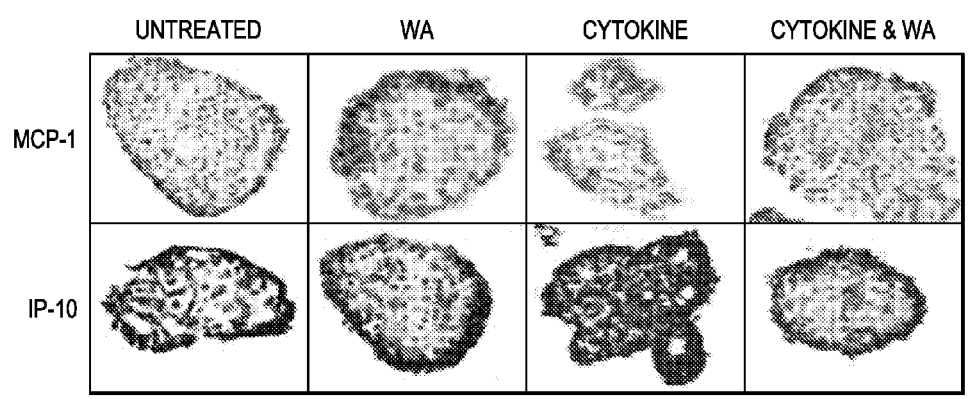

FIGS. 3A-3C show the detection of the inhibitory effects of Withaferin A at protein level. Even though, Withaferin A showed effective inhibition of the inflammatory genes at transcription level, RT-PCR data could not reflect the actual protein level. The protein levels of MCP-1 reported to be crucial for islet cell loss and IP-10, the most abundantly expressed protein after cytokine stimulation by histochemical staining were also evaluated. As shown in FIG. 3B, cytokine treatment strongly stimulated the expression of MCP-1 and IP10. Treatment with Withaferin A alone showed a level of expression similar to untreated islets. Withaferin A and cytokine treatment decreased the intensity of MCP-1 staining and IP-10 staining, indicating a much lower protein level as compared to cytokine treatment. The IP-10 expression level was examined by flow cytometry. After treatment, islets were fixed, permeablized and aliquoted to three tubes staining with anti-IP10. The peak of cytokine treated islets shifted to the right as compared to untreated islets indicating strong induction. The presence of Withaferin A made the peak moved back to left indicating inhibition of the induction but not completely overlapping with the original peak. FIG. 3A illustrates the mean channel fluorescence data showed that an increase from 4214.15 (+/−80.83) to 18024.08 (+/−375.42) when islets were treated with the cytokine mix. Withaferin A treatment decreased the fluorescence intensity to 7318.94 (+/−78.21).

Figure 4B:
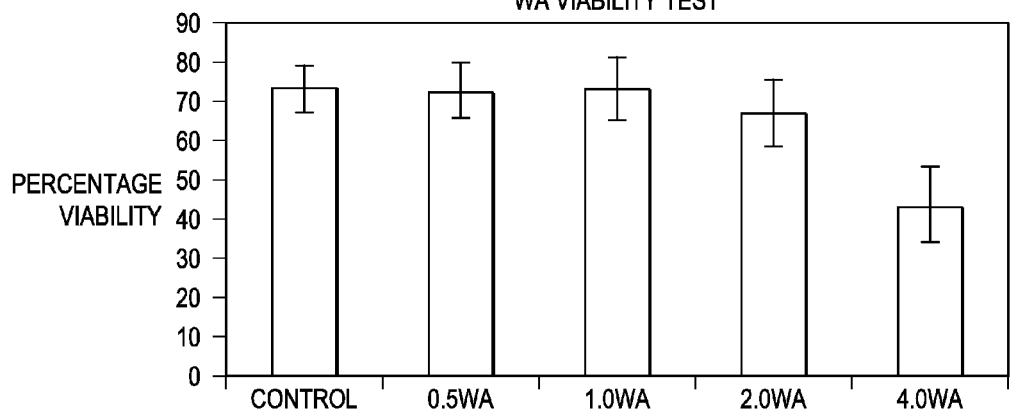
Figure 4C:
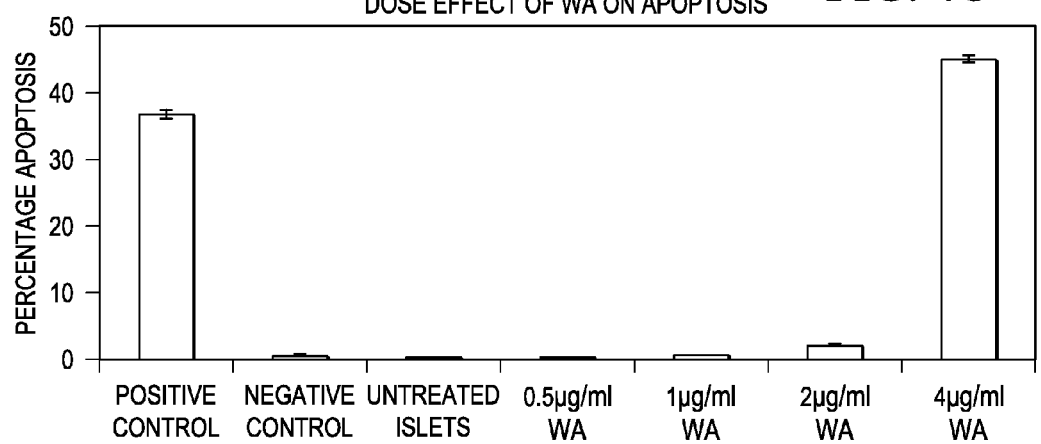
Figure 4D:
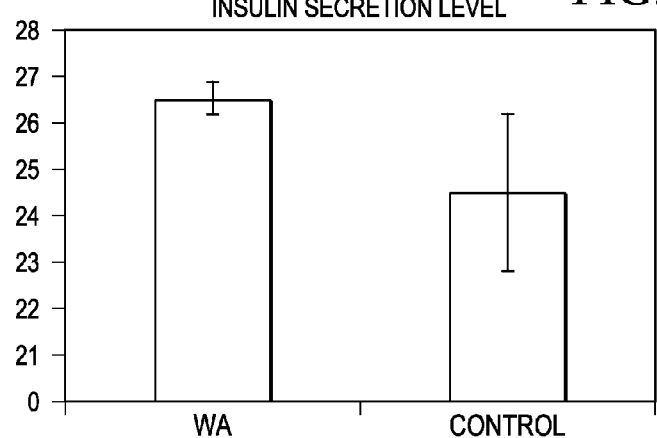

Effect of Withaferin A on islet quality: As a potential anti-inflammatory agent for use in islet cell transplantation, it is important to evaluate whether Withaferin A has a harmful effect on islet cell function. The present inventors conducted a dose effect study of Withaferin A on islets. A high dose of Withaferin A could decrease the cell viability. The viability and apoptosis test of islet with four different concentrations of Withaferin A (0.5 μg/mL, 1 μg/mL, 2 μg/mL and 4 μg/mL) was examined. FDA/PI staining was used to determine the islet viability. After 48 hours culture, islet viability was not decreased in the presence of 0.5 μg/mL and 1 μg/mL Withaferin A. A slight decrease of viability is observed with 2 μg/mL Withaferin A. A significant loss is observed in 4 μg/mL Withaferin A treated islets. (FIG. 4B) These data demonstrated that the concentration of 1 μg/mL Withaferin A which was used in this study did not affect the viability of islets. To further confirm this, a TUNEL assay was performed with same concentration of Withaferin A. A slight shift of 2 μg/mL Withaferin A treated sample was observed and a second peak which indicated apoptosis cells emerged in the 4 μg/mL Withaferin A treated sample. 0.5 μg/mL and 1 μg/mL Withaferin A treated samples overlapped well with untreated islets. (FIG. 4A) The percentage of FITC positive population (apoptosis cells) was close to zero among untreated and low Withaferin A dose samples. A small increase in FITC positive population occurred in 2 μg/mL Withaferin A sample, and a dramatic increase was observed in 4 μg/mL Withaferin A sample. (FIG. 4C). The inventors also tested the islet viability in the presence of both cytokine mix and Withaferin A. The result showed no difference between two conditions. (data not shown). Since 1 μg/mL Withaferin A is the highest dose examined and proved to be of no harm to islet, the inventors used this dose to test the islet potency by static incubation. Stimulation Index in Withaferin A treated group has no significant difference when compared to control group which indicated that 1 μg/mL Withaferin A was not harmful to islet cell function (FIG. 4D).

The findings of the studies conducted in the present invention are presented and discussed herein below.

Figure 5A:
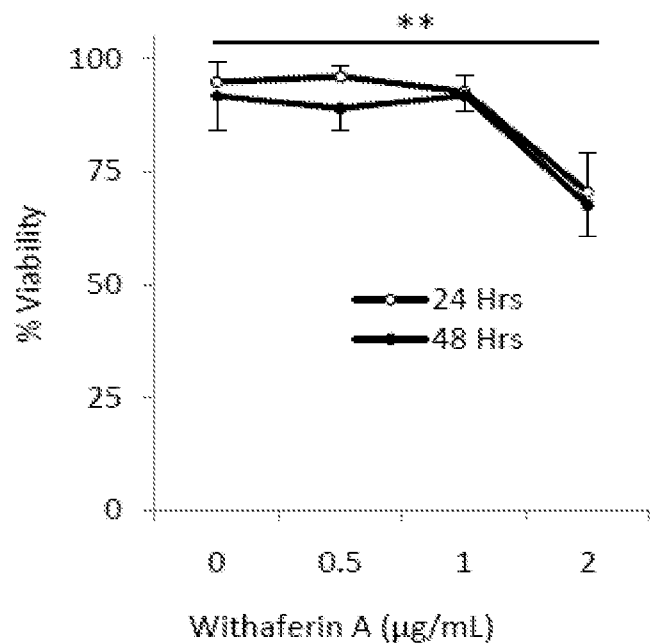
FIGS. 5A-5D show the optimal Withaferin A dosing is found without toxicity to islets: Human (5A and 5B) and mouse (5C and 5D) islets were cultured with Withaferin A. Samples were taken at 24 and 48 hours and stained with Hoechst 342 (all nuclei) and propidium iodide (necrotic nuclei). The percent viability was determined as the $PI^+$ area subtracted from the total area (Hoe342 stained). The optimal Withaferin A dose was determined to be 1.0 µg/mL Withaferin A for human islets (5A) and 0.5 µg/mL for mouse islets (5C). Asterisks above bars indicate statistically significant differences in mean values (*$p<0.05$ for 48 h and **$p<0.001$ for 24 and 48 hours) between controls and islets exposed to Withaferin A based on two-tailed Student's t test; N=10.
Figure 5B:
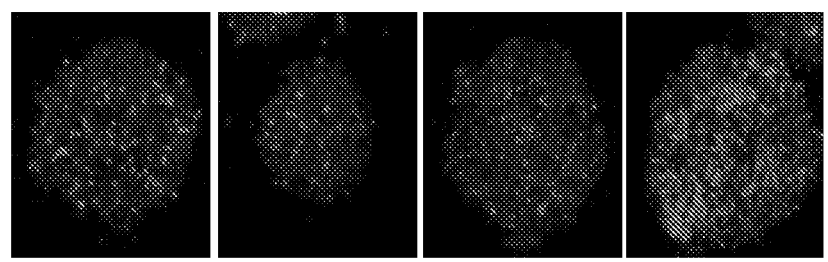
Figure 5C:
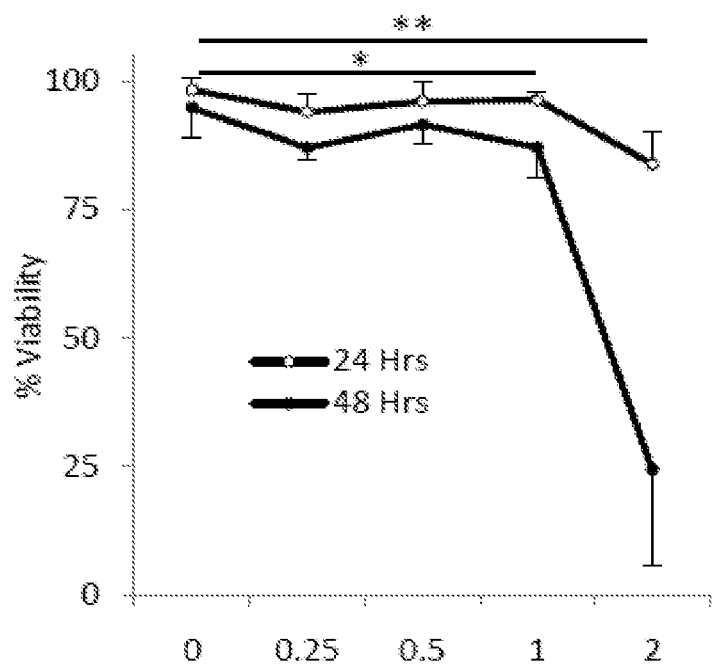
Figure 5D:
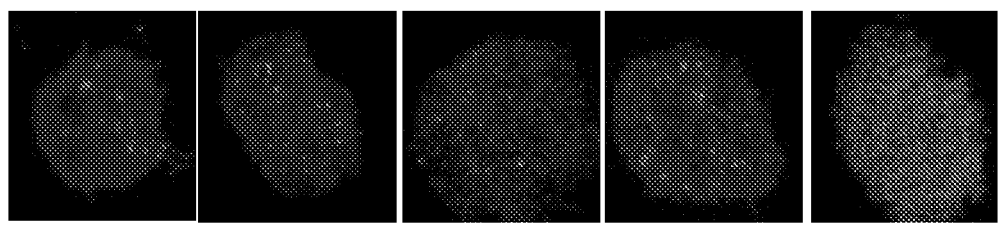

Withaferin A can be cultured with human and mouse islets without causing toxicity: Since Withaferin A has been used to treat cancer, it is important to establish a dose of this agent that optimally inhibits NF-κB without leading to decreased viability or function, as described previously. Previous findings presented hereinabove indicated that 1 μg/mL Withaferin A was not harmful to islet cell function, so in order to determine the accurate detrimental dose of Withaferin A, the inventors cultured Withaferin A with human islets from three separate pancreas isolations and mouse islets from multiple donors. After only 24 hours, 2.0 μg/mL Withaferin A caused a significant decrease in viability of human islets (FIG. 5A) compared to control islets (70.5±8.8% vs. 94.9±4.5%, p<0.0001). However, after 48 hours, there was no noticeable difference between control (91.8±7.4%) and not only 0.5 μg/mL Withaferin A (89.0±4.6% p=0.36), but also 1.0 μg/mL Withaferin A (91.9±3.5%, p=0.87). For mouse islets (FIG. 5B), viability significantly decreased with 1.0 μg/mL Withaferin A compared to control (87.8±11.1% vs. 97.3±2.2%, p<0.05). At 48 hours, there was no significant difference in viability between the control (93.8±8.0%) and either 0.25 μg/mL Withaferin A (90.1±6.6%, p=0.25) or 0.5 μg/mL Withaferin A (94.6±4.4%, p=0.77). Furthermore, the insulin secretion function of islets was determined after co-culture with Withaferin A. There was no significant difference in stimulation index between control human islets (3.11±1.53) or islets cultured with 0.5 (3.52±1.97, p=0.10) or 1.0 μg/mL Withaferin A (4.21±0.41, p=0.51) after 24 hours. Similarly, mouse islets showed no significant difference in stimulation index after 24 hours between control (11.13±9.28) and islets treated with 0.5 μg/mL Withaferin A (7.05±2.20, p=0.30) as seen in FIG. 5D. These data confirm the previous findings presented herein that Withaferin A has no deleterious effect on the viability or potency of human islets at 1.0 μg/mL or on the viability of mouse islets at a concentration of 0.5 μg/mL (FIG. 5C).

Figure 6A:
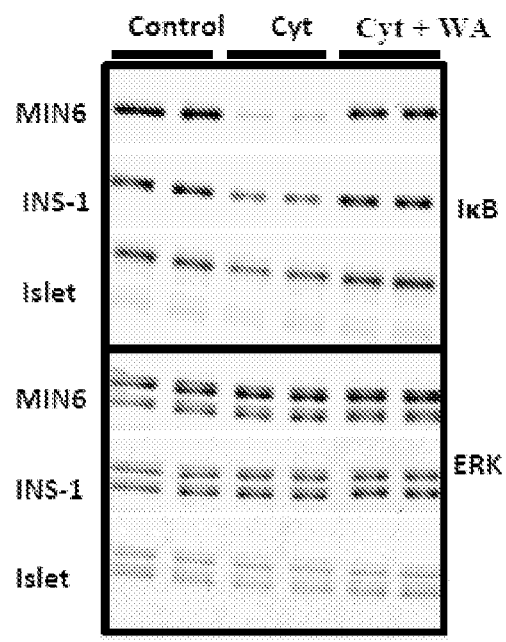
FIGS. 6A and 6B show the effect of cytokine cocktail on IκB in islets and β cells: Immunoblot analysis (6A) of IκB protein in human islets and β-cell lines treated with a cytokine (Cyt) cocktail of IL-1β (50 U/mL), TNF-α (1000 U/mL), and IFN-γ (1000 U/mL) for 20 min in the presence or absence of Withaferin A. Runs were repeated twice and performed in duplicate. Graphical representations (6B) are expressed as means±STD. Asterisks above bars indicate statistically significant differences in mean values (*$p<0.05$, $p<0.01$, *$p<0.001$) between treatments and controls (black bars) for each cell type based on two-tailed Student's t test.
Figure 6B:
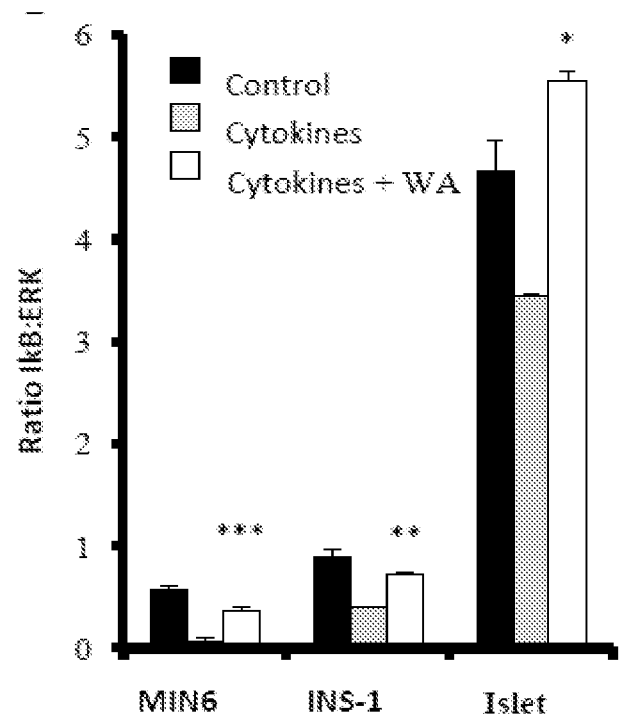

Withaferin prevents degradation of Inhibitor of κB (IκB) protein when islets and β cells are exposed to cytokines: Inflammation elicited by immune cells requires the activation of nuclear factor kappa-light-chain-enhancer of activated B cells (NF-κB).[18-20] NF-κB is activated as a direct result of phosphorylation and rapid degradation of inhibitory IκB protein.[20,21] In order to identify effects of cytokines on NFκB signaling in islets, the inventors analyzed effects of IL-1β, TNF-α, and IFN-γ cytokine cocktail on IκB in human islets and β-cells lines. In response to cytokine cocktail, IκB was rapidly reduced (up to 90%) relative to ERK1/2 expression (FIGS. 6A and 6B). In each case, Withaferin A prevented the reduction of IκB, indicating that it opposes NF-κB activation in islets and β cells. Overall the data suggest that Withaferin A may protect pancreatic islets by countering cytokine-induced cytokine gene expression and by suppressing the activation of NF-κB.

Figure 7A:
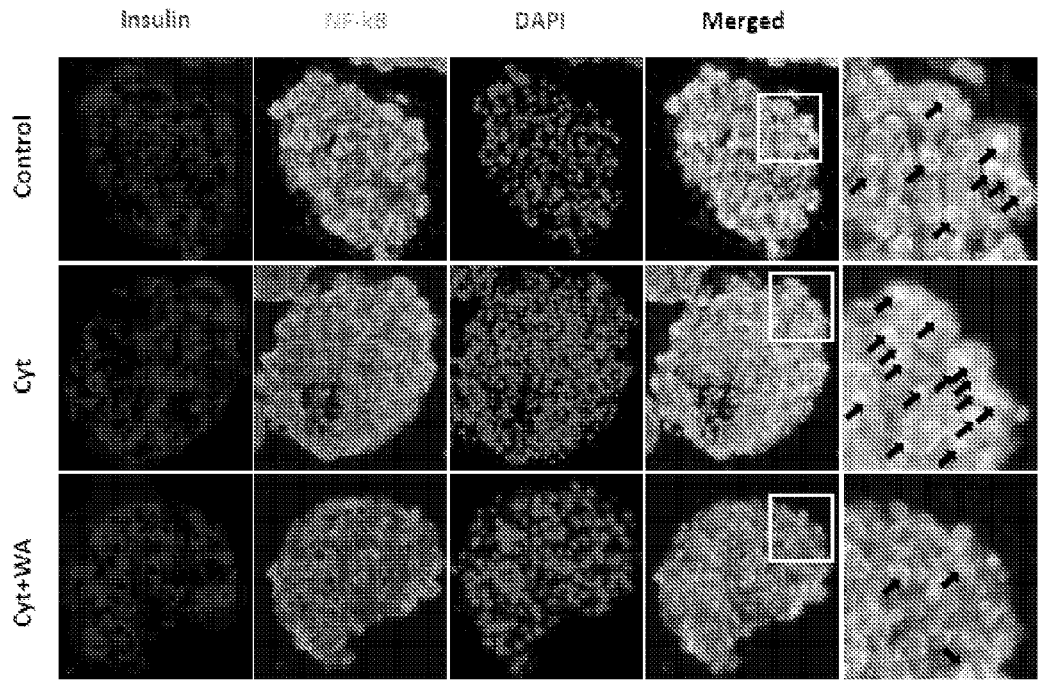
FIGS. 7A and 7B show NF-κB nuclear translocation inhibited by Withaferin A: Human islets (7A) were exposed to the cytokine cocktail with or without Withaferin A for 24 hours, then islets were fixed in formalin, embedded in paraffin, sectioned, then underwent heat-mediated antigen retrieval for 20 minutes before being probed for insulin (A, blue), NF-κB p65 (A, green), and for nuclei (pseudocolored-red). Merged nuclear and NF-κB staining revealed translocation with a yellow color (indicated by black arrows). Manual counting of at least 250 insulin positive nuclei for NF-κB translocation revealed that 0.5 µg/mL Withaferin A significantly inhibits NF-κB activation down to control levels, and 1.0 µg/mL Withaferin A decreases NF-κB translocation to below control levels. Graphical representations (7B) are expressed as means±STD. Asterisks above bars indicate significant differences in mean values (*$p<0.05$) as determined by Turkey-Kramer post-hoc tests.
Figure 7B:
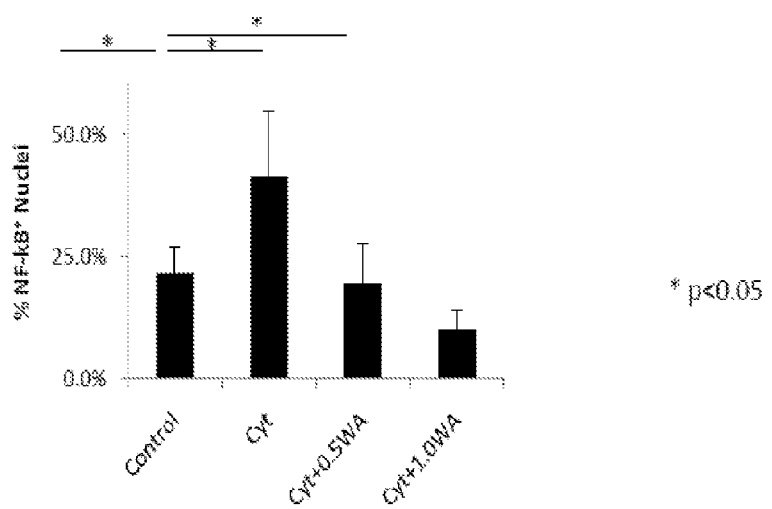
Figure 10A:
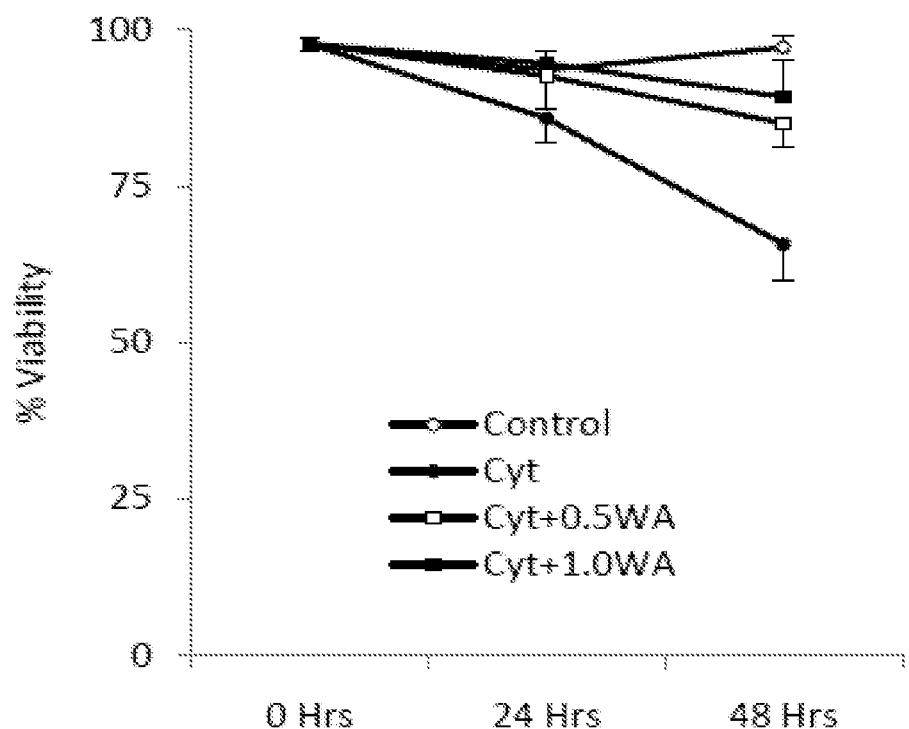
FIGS. 10A-10H show that Withaferin A protects human and mouse islets from inflammatory cytokine-mediated necrosis and apoptosis: Human (10A) and mouse (10B) islets were incubated with the inflammatory cytokine cocktail for 24 and 48 hours with or without Withaferin A. Islets were recovered and viability was assessed by Hoe342/PI nuclear staining (10C and 10D). Islets were protected from cytokine damage by Withaferin A at both time points. Islet potency was assessed by stimulation index after 24 hours. Human islet potency was significantly decreased by cytokine, but adding Withaferin A yielded a stimulation index value greater than control. Mouse islet potency was also protected by adding Withaferin A. Then cytokine mediated beta cell apoptosis was confirmed by TUNEL staining Human islets probed for insulin (H, red) and apoptotic nuclei (H, green). Manual counting of more than 250 nuclei revealed higher levels of apoptosis when islets were exposed to cytokines, which was significantly reduced by the addition of Withaferin A (10G), which returned apoptosis levels to control levels (1.0 µg/mL Withaferin A). Graphical representations (10E-10G) are expressed as means±STD. Significant differences between mean values groups as determined by Turkey-Kramer post-hoc tests are indicated by an asterisk (*p<0.05) above bars.
Figure 10B:
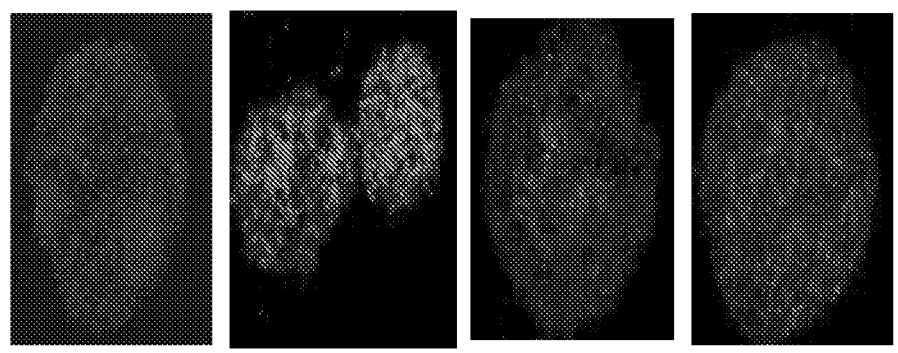
Figure 10C:
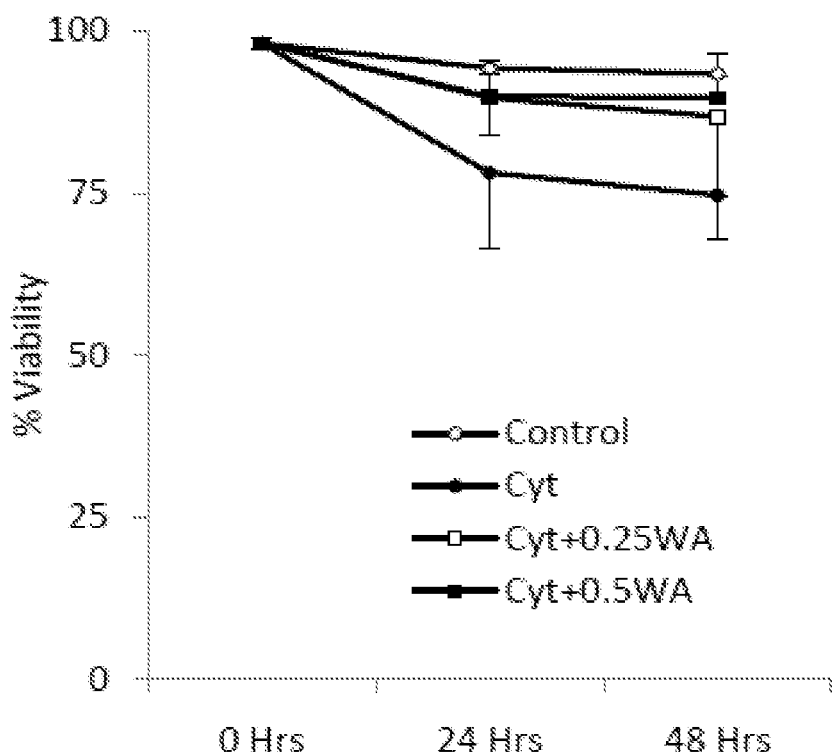
Figure 10D:
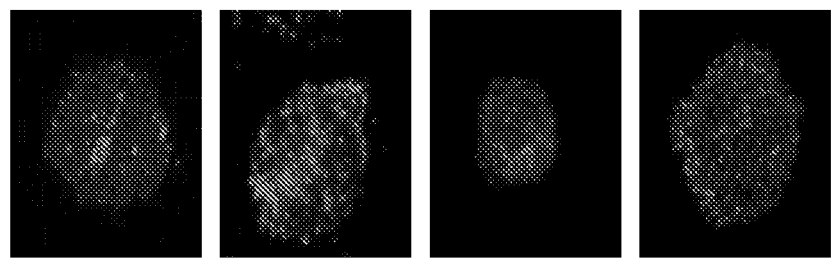
Figure 10E:
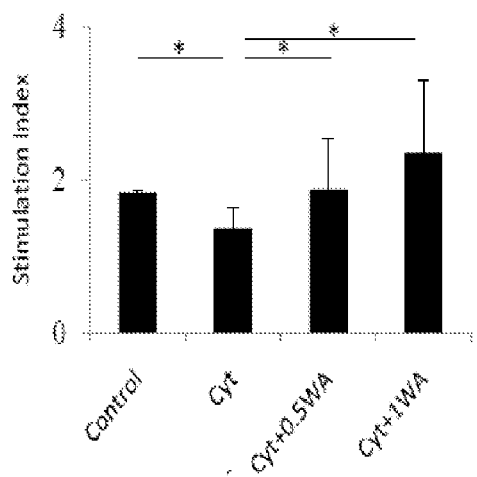
Figure 10F:
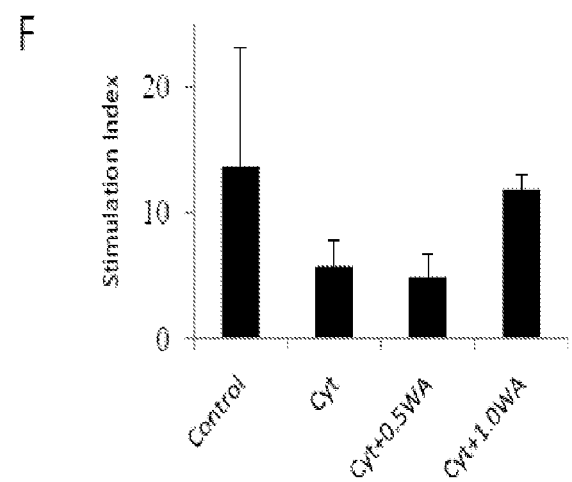
Figure 10G:
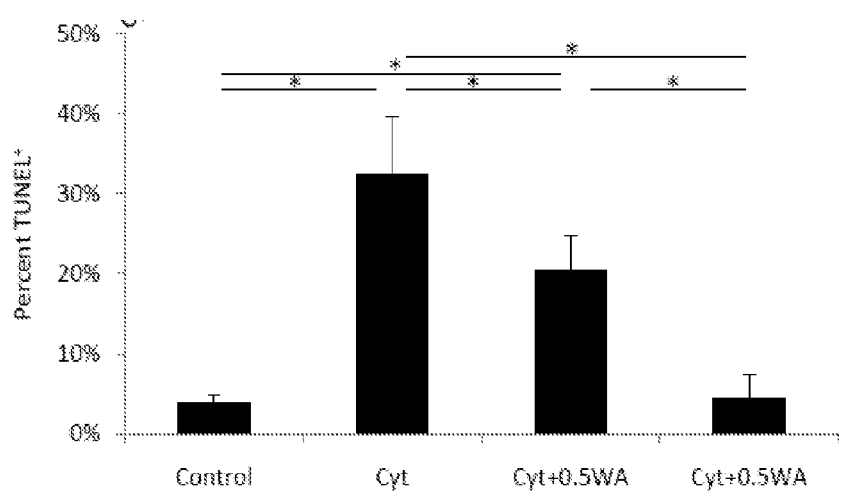
Figure 10H:
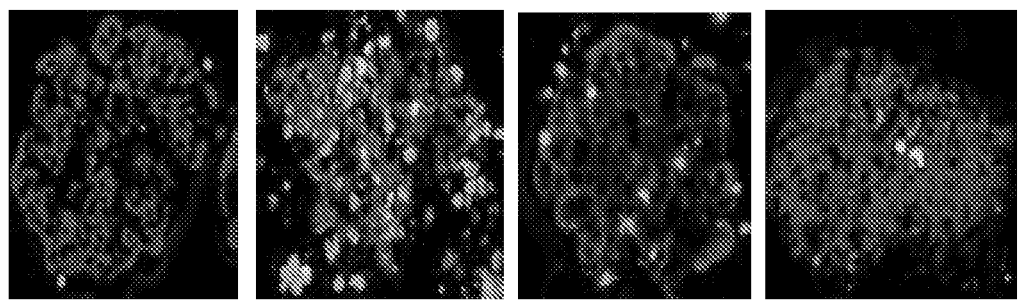
Figure 11A:
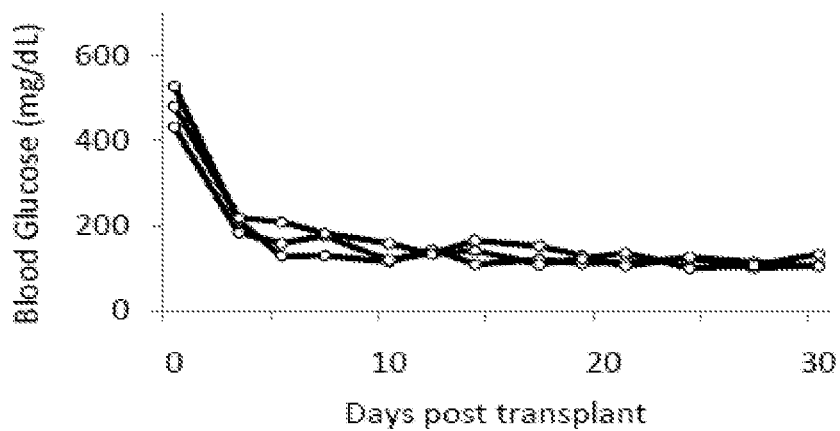
Figure 11B:
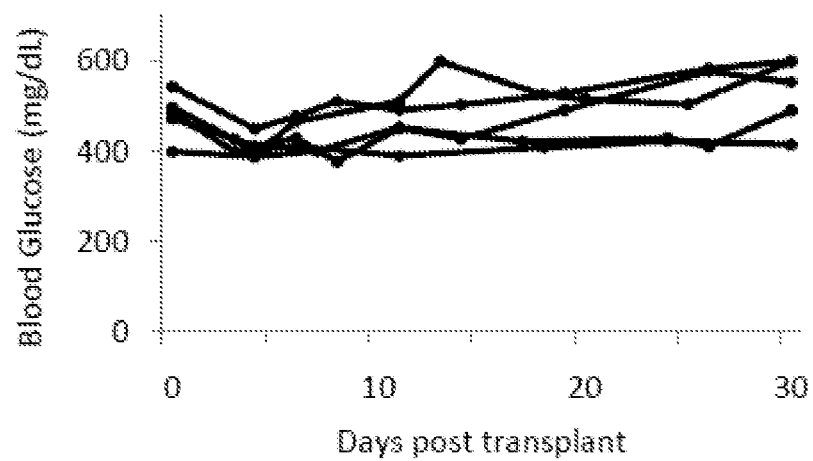
Figure 11C:
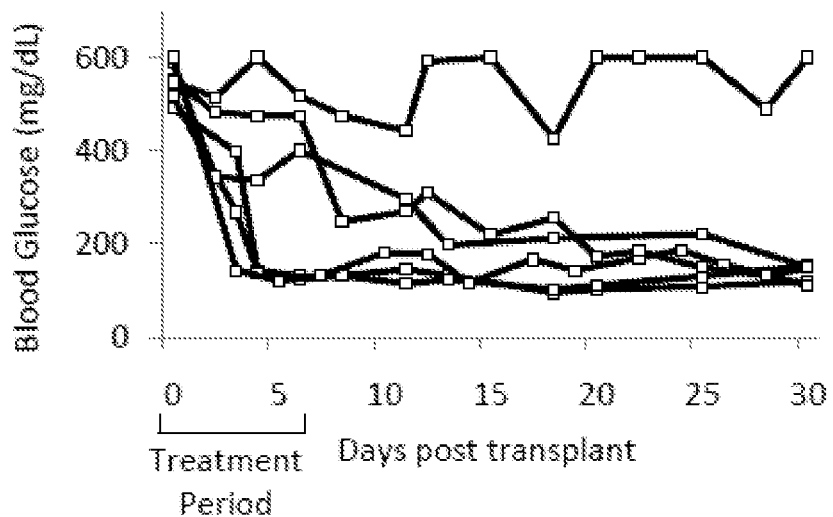
Figure 11D:
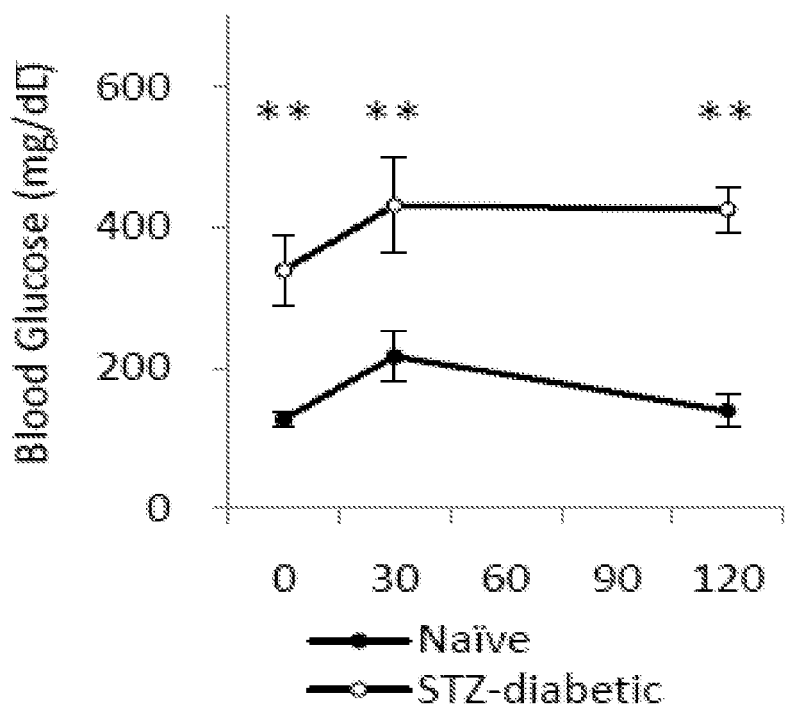

NF-κB translocation in human β cells is inhibited by Withaferin A: After the inhibitory unit, IκB is degraded, the NF-κB heterodimeric transcription factor consisting of p50 and p65 moves to the nucleus in a process known as nuclear translocation.[20] At this stage, NF-κB begins its effector role, promoting transcription of inflammatory related genes. To determine whether NF-κB has been activated and moved to the nucleus, immunohistochemistry was performed to locate the p65 portion of NF-κB as described elsewhere.[12] All nuclei in insulin positive human β cells were counted and when NF-κB was stained in the nucleus it was classified NF-κB+ and nuclei without NF-κB were classified NF-κB- (FIG. 7A). Percent NF-κB activation was measured at 24 hours after culture with the cytokine cocktail and Withaferin A (FIG. 7B). Control islets constituently express NF-κB in 21.6±5.3% of β cells, whereas this number was doubled to 41.3±13.5% by adding cytokines The addition of 0.5 μg/mL Withaferin A returned NF-κB activation back to control levels with 19.5±8.1% of insulin positive cells being NF-κB+. However adding 1.0 μg/mL Withaferin A to human islets exposed to the cytokine cocktail reduced the percent NF-κB+ cells to 10.0±4.1%, which is half the control level and four times lower than cytokine stimulated β cells. Statistical analysis by ANOVA determined that there was a significant difference (p<0.05) between each group except between Control and Cyt+0.5 Withaferin A. These results demonstrate potent NF-κB inhibition by Withaferin A at levels that are physiologically damaging to islets.

Inflammatory cytokine and chemokine secretion by islets is inhibited by Withaferin A: After NF-κB has been activated, it leads to the transcription of several inflammatory cytokines and chemokines; previous study by the present inventors have shown that mRNA levels of several cytokines and chemokines were decreased by the addition of Withaferin A.[17] Although this is an important observation, it is vital that the physiological effect on the extracellular environment is evaluated by measuring secreted cytokine and chemokine levels, because many of these chemokines such as IP-10 or MCP-1 cause macrophage or monocyte chemotactaxis towards the newly engrafted islets and activation of other immune cells. In this study cell culture supernatants from human islets exposed to cytokines and Withaferin A was evaluated by a multiplex bead assay using Luminex® technology. The cell culture supernatant from which the samples were taken for Luminex analysis contained fifty, pure, hand-picked human islets, which had been cultured at 22° C. for over a week to decrease resident macrophage numbers that might interfere (N=10).

Previous studies have shown that NF-κB is implicated in the transcription of G-CSF, IL-2, IL-6, IL-8, IP-10, MCP-1, IL-1α, TNF-α, MIP-1α, and MIP-1β.[23-27] These cytokines and chemokines also play a strong role in inflammation and immune cell activation, so their secreted levels were measured. Treatment with Withaferin A decreased secreted levels of each molecule (FIGS. 8A-8H), and use of 1.0 μg/mL Withaferin A caused a significant decrease in secreted inflammatory molecules in each case (p<0.05). These data demonstrate the ability of Withaferin A to not only decrease cellular activity of NF-κB, but also to decrease secreted levels of associated pro-inflammatory and chemotactic cytokines and chemokines Increased MCP-1 and IP-10 production induced by cytokines is localized to islets and is reduced by Withaferin A: Beta cells are programmed to typically create insulin and not cytokines, so to further confirm the origin of these inflammatory mediators, immunohistochemical analysis was performed on formalin fixed, paraffin embedded human islets. Staining of IP-10, MCP-1, and Insulin was performed to confirm the stimulated expression and subsequent inhibition by Withaferin A in beta cells. Staining conditions (time, temperature, washing, and antibody) and fluorescent micrograph capture conditions (exposure time, background correction, file type and size, etc.) for each treatment group was held constant, and mean protein concentrations per islet were quantitatively determined by measuring the mean fluorescent intensity of insulin positive areas by Image J (NIH, Bethesda, Md.) as described previously.[28] This analysis showed that IP-10 and MCP-1 levels were both increased within beta cells by cytokine treatment, but Withaferin A was able to decrease this level to near control levels (FIGS. 9A and 9B).

Withaferin A protects human and mouse islets from cytokine-induced damage, and preserves islet potency: In addition to studying the effect of cytokines on the inflammatory mediators produced, it is of the utmost importance to evaluate the viability and functionality of the islets after being exposed to inflammatory cytokines. Thus, islet cell necrosis, apoptosis, and potency were each evaluated after exposure to cytokines with or without Withaferin A.

Cytokines significantly increased islet cell necrosis at 24 hours compared to control levels in both human (viability: 85.8±3.9% vs. 93.5±3.2%, p<0.05) and mouse (viability: 78.1±11.6% vs. 93.3±2.9%, p<0.05) islets. Withaferin A prevented this damage as evidenced by a significant difference between both doses of Withaferin A and cytokines without any significant difference between Withaferin A treatment and control levels for both human (92.6±5.1% and 94.6±2.9% for 0.5 and 1.0 μg/mL Withaferin A respectively; p<0.05 vs. cytokines, p>0.05 vs. control) and mouse islets (89.7±5.9% and 89.9±3.6% for 0.25 and 0.5 μg/mL Withaferin A respectively; p<0.05 vs. cytokines, p>0.05 vs. control). After 48 hours, this same pattern of Withaferin A protection was seen in mouse islets, but after 48 hours there was a significant difference between each treatment group in human islets. Additionally, apoptosis was increased from cytokine treatment as evidenced by increased TUNEL positive staining in human β cells. At twenty four hours, there was a significant difference between each treatment group (FIGS. 10A-10H) except between control versus cytokine+1.0 μg/mL Withaferin A, which demonstrates that Withaferin A can totally cancel any effect of cytokines on β cell apoptosis.

Evaluation of the insulin secretion ability of human islets after twenty four hours showed that cytokines significantly decreased the stimulation index compared to control (1.59±0.34 vs. 3.10±1.53, p<0.05). However, 1.0 μg/mL Withaferin A significantly increased the stimulation index compared to cytokines alone (2.20±0.61, p<0.05), and showed no significant difference compared to control islets (p>0.05). Stimulation index levels for mouse islets at the same timepoint did not show any significant differences.

Immediate graft loss is reduced in Intraportal Islet Transplantation by Withaferin A mediated NF-κB blockade: The most important evaluation for islet transplantation is the in vivo assay. To determine only the anti-inflammatory effects of Withaferin A on islet transplantation, a syngeneic model was used. In this model, only immediate inflammatory response of the innate immune system affects graft rejection, rather than any autoimmune or alloimmune responses. Successful islet transplantation was defined as reduction of diabetes by normoglycemia. It was determined that 400 islets are required for successful transplantation into the portal vein of the liver for mice. Using only half that number of islets with vehicle injection results in a 0% success rate, thus 200 islets is a sub-optimal dose incapable of curing diabetes (FIGS. 11A-11G).

Daily intraperitoneal injections of Withaferin A (25 μg, 0.5 mL/mouse) for seven days post-transplant beginning immediately after islet infusion were performed on six mice. The addition of Withaferin A to the post-operative treatment led to amelioration of diabetes in 5/6 mice (83%) with infusion of a suboptimal dose of 200 islets. To evaluate the islet graft function, IPGTT was performed on cured mice and vehicle treated mice on day 30. To control for the pattern in islet function, naïve and STZ-induced diabetic mice were tested as well. After 12 to 14 hours of fasting, mice were injected with a 5% glucose solution (2 mg/kg body weight) and blood sugar levels were measured at zero, thirty, and one hundred twenty minutes after the injection. After injection, blood glucose levels increase with stabilization below 200 mg/dL as seen in functional normal mice. This same pattern is seen in the Withaferin A-treated mice, which showed a significant difference for each time point compared to the vehicle treated mice (150.3±89.2 vs. 485±95.4 mg/dL glucose for 0 minutes, p<0.0005; 267.8±84.8 vs. 523.8±95.3 mg/dL glucose for 30 minutes, p<0.005; 155.7±81.2 vs. 472.8±101.8 mg/dL glucose for 120 minutes, p<0.0005). This shows that mice receiving Withaferin A post-transplant had a sufficient islet mass to be functional and comparable to naïve mice.

Inflammation plays an important role in T1DM and islet cell transplantation failure. Cytokine induced inflammatory genes expression in islet cells is one of the major components of this inflammation response. In this study, the inventors confirmed that IP-10, RANTES, MCP-1, IL-1beta, MIG, iNOS and other inflammatory genes are upregulated in insulin producing cells upon cytokine stimulation. Chemokines such as IP10, MIG, RANTES, and MCP-1 can attract various immune cells including macrophages, T-cells, NK cells and dendritic cells which are responsible for both short term and long term islet cell loss. IL-1beta to which that islet cells are very sensitive is one of the constituents tested in the cytokine mix of the present invention. A lower dose of IL-1beta is sufficient in inducing apoptosis and inflammation response. The human islet data confirmed this cytokine is able to induce the expression of itself in islet cells which can further amplify its effect. Another important gene included in this study iNOS is also reported to be crucial for islet damage. Nitrite oxide produced by iNOS is recognized as a major apoptosis inducer for beta cells.

Pancreatic islets are exposed to the damaging and inflammatory effects of cytokines in the early period post-transplantation. In this early inflammatory period, several pro-inflammatory cytokines such as TNF-α, IFN-γ and IL-1β exert a damaging effect through different receptors. Rather than attempting to target each cytokine or each receptor, it is more effective to specifically target a common downstream signaling pathway transcription factor where pro-inflammatory signals bottleneck; one such target is NF-κB. Activation of NF-κB in β cells and islets by a cytokine cocktail was potently inhibited by Withaferin A as demonstrated by the prevention of both IκB degradation and NF-κB nuclear translocation. The present invention demonstrates that islets contribute to the inflammatory response by secreting pro-inflammatory cytokines and chemokines which is inhibited by Withaferin A. Immunohistochemistry also demonstrated that the origin of these pro-inflammatory molecules was from insulin positive islets themselves and not merely resident macrophages. Additionally, it was found that Withaferin A prevents cytokine induced necrotic and apoptotic cell death in islets. Withaferin treatment has led to significant improvement in graft survival and function for intraportal islet transplantation. Inhibition of NF-κB by Withaferin A can counteract the cytokine mediated inflammatory response in islets and subsequent graft destruction.

Multiple doses of Withaferin A ranging from 2.5 to 50 μg/mouse were tested in an in vivo mouse model, and 25 μg was found to be the ideal dose. Considering that mice have an approximate blood volume of 2.5 mL, the concentration of Withaferin A in the mouse was approximately ten times greater than in the in vitro model. This has often been found to be necessary for animal models, since both the liver and kidneys metabolize and remove biological agents.

Although NF-κB has been predominantly studied in relation to the inflammatory events related to type 1 diabetes, its role in islet transplantation has received little attention. This study demonstrates that cytokine stimulation causes production and secretion of several inflammatory cytokines and chemokines by islets themselves, attracting effector cells of the innate immune system such as neutrophils, monocytes, and macrophages, mediating graft rejection. The present study showed that several important cytokines and chemokines such as MCP-1, IP-10, IL-6, IL-8, G-CSF, MIP-1α, MIP-1β, IL-1a and IL-2 were secreted by islets after exposure to cytokines. It has been reported that transcription of these molecules is mediated by NF-κB.[23-27] Thus, it follows that inhibition of NF-κB would decrease the levels of these molecules. This hypothesis was confirmed by multiplex analysis of several cytokines revealing that Withaferin A inhibited production of these pro-inflammatory cytokines in a dose dependant manner. It was also somewhat unexpected that beta cells would produce such levels of cytokines and chemokines, because they are specialized to produce insulin not inflammatory mediators. Immunohistochemical staining demonstrated the clear co-expression of insulin along with IP-10 and MCP-1. Also, the islets used for the multiplex assay were cultured for over a week at 22° C. to reduce the interference from resident macrophages. These insights into the beta cell inflammatory reaction are substantiated by other reports demonstrating increased production of MCP-1 and IL-8 by islets under stimulation by IL-1β and lipo-polysaccharide.[9] Even if some resident macrophages were responsible for the cytokines and chemokines secreted, their presence and inhibition is a factor of islet transplantation that is relevant to the immediate inflammatory reaction.

All of the mouse data analyzed supports the findings in studies performed in human islets, so it follows that the results obtained in then present invention from the intraportal isograft augmented with Withaferin A has clinically relevant applications in humans[29,30].

A recent study of an IKK-beta inhibitor found that the same set of cytokines did not affect cell death in islets[8], but several other reports support our findings that cytokines cause cell death in islet and beta cells.[31,32] One of these reports[32] found that oxygen free radicals played a role in cytokine mediate damage; Withaferin A has anti-oxidant properties, which could additionally protect islets from oxidative damage. Another more recent report emphasizes the importance of NF-κB inhibition when islets are exposed to cytokines, but this study uses a degradation resistant IκBα transgenic mouse.[33] This and other studies have pursued genetic manipulation to show improved islet function with genetically induced NF-κB inhibition; however, this strategy is not easily applied to the clinical setting. The advantage of Withaferin A is that it could more easily be incorporated into an immunosuppressive regimen to trigger effective NF-κB inhibition, preventing damage to islets by inflammatory cytokines.

The composition of the present invention may be used in a method of treating and may be administered using a variety of methods, parenterally, intraperitoneally, intraspinally, intravenously, intramuscularly, intravaginally, subcutaneously, or intracerebrally. Dispersions may be prepared in glycerol, liquid polyethylene glycols, and mixtures thereof and in oils. Compositions suitable for injectable use include sterile aqueous solutions (where water soluble) or dispersions and sterile powders for the extemporaneous preparation of sterile injectable solutions or dispersion. The composition may be sterile and a fluid to the extent that easy syringability exists. It may be stable under the conditions of manufacture and storage and may be preserved against the contaminating action of microorganisms such as bacteria and fungi. The carrier may be a solvent or dispersion medium containing, e.g., water, ethanol, poly-ol (e.g., glycerol, propylene glycol, and liquid polyethylene glycol, and the like), suitable mixtures thereof, and vegetable oils. The proper fluidity may be maintained, by the use of a coating such as lecithin, by the maintenance of the required particle size in the case of dispersion and by the use of surfactants. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin. The composition of the present invention may be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied as will be known to the skilled artisan. The amount of the therapeutic compound in such therapeutically useful compositions is such that a suitable dosage will be obtained. Parenteral compositions in dosage unit form for ease of administration and uniformity of dosage may also be used. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on the unique characteristics of the therapeutic compound and the particular therapeutic effect to be achieved, and the limitations inherent in the art of compounding such a therapeutic compound for the treatment of a selected condition in a subject. Aqueous compositions of the present invention may include an effective amount of the coating, e.g., nanoparticle, nanofibril or nanoshell or chemical composition for use with the present invention dissolved and/or dispersed in a pharmaceutically acceptable carrier and/or aqueous medium. The composition of the present invention may generally be formulated for parenteral administration, e.g., formulated for injection via the intravenous, intramuscular, sub-cutaneous, intralesional, and/or even intraperitoneal routes. The preparation of an aqueous compositions that contain an effective amount of the nanoshell composition as an active component and/or ingredient will be known to those of skill in the art in light of the present disclosure. Typically, such compositions may be prepared as injectables, either as liquid solutions and/or suspensions; solid forms suitable for using to prepare solutions and/or suspensions upon the addition of a liquid prior to injection may also be prepared; and/or the preparations may also be emulsified.

In some instances, the composition of the present invention may be administered to the patient before the transplant, during the transplant, after the transplant, or combinations thereof. In addition, the islet cells may be treated with the Withaferin A composition prior to transplantation, before the transplant, during the transplant, after the transplant, or combinations thereof and pig islets and or human islets may be used.

For example, the Withaferin A composition may be administered to a patient during the transplant and after the transplant on day 0 through day 7. This is only one embodiment and the skilled artisan can adjust the time of administration as necessary given the specific characteristics. In this example, the method of administering is subcutaneously and can be in the form of an injection or an automated delivery mechanism (e.g., pump). Again a sample dosage is about 5-10 mg but may be 1-5, 5-12, 10-15, 12-18, 15-20, 25 or more given the specific characteristics and the advice of the skilled artisan. In addition to being used alone, Withaferin A can be part of an immunosuppressive regimen that combines various other active agents (e.g., Prograf (tacrolimus) and Mycophenolic Acid) to aid in the islet transplantation.

Withaferin A is able to inhibit iNOS expression and NO synthesis in macrophages cell line. It is also reported that IL-6, IL-8 and TNF-alpha expression is inhibited by Withaferin A treatment in different types of cells. Reduced adhesion of monocytes was reported in one of these studies. This could be beneficial in islet cell transplantation since it may alleviate the exposure of islet cells to immune cells.

This study demonstrated the efficacy of Withaferin A as a novel anti-inflammatory agent and NF-κB inhibitor that mediates improved intraportal graft survival in pancreatic islet transplantation by counteracting the immediate cytokine mediated inflammatory reaction. This process leads to attrition of a substantial portion of the islet mass. By preventing the damaging effects of this inflammatory reaction, more islets survive leading to euglycemia in marginal islet infusions. Hypothetically, if half the graft mass was protected from destruction, then the longevity of islet function could be doubled. This implication has significant ramifications for islet transplantation where it is often difficult to achieve sustained insulin independence with one donor pancreas. Also, hypoxic damage, which islets are very sensitive to during the isolation process and early transplant period, is an activator of NF-κB, so Withaferin A could also be applied to prevent hypoxic islet cell damage. Since NF-κB activation is also a primary part of immune cell activation, the use of Withaferin A could be used to prevent the activation of macrophages, neutrophil, and monocytes. Also, since it was found that Withaferin A inhibited IL-2 production, this could decrease T-cell activation.

Therefore, the results for Withaferin A treatment are particularly surprising, and provide an unexpected alternative for islet cell protection. Data from this study showed that at proper concentration, Withaferin A can successfully reduce the induction of inflammatory genes after cytokine exposure without affecting the viability and potency of islet cells. This property of Withaferin A makes it a potential additive to immunosuppressive regimen in islet cell transplantation.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Pat. No. 7,695,718: Methods for the Treatment of IL-1β Related Diseases.
U.S. Patent Publication No. 20090093434: Use of EIF-5A1 siRNA to Protect Islets Cells from Apoptosis and to Preserve their Functionality.
U.S. Patent Publication No. 20110008343: Method of Reducing Tissue Loss in Pancreatic Islet Cell Transplantation.
1. Bennet W, Groth C G, Larsson R, Nilsson B, Korsgren O. Isolated human islets trigger an instant blood mediated inflammatory reaction: implications for intraportal islet transplantation as a treatment for patients with type 1 diabetes. Ups J Med Sci. 2000; 105 (2): 125-33.
2. Bennet W, Sundberg B, Groth C G, et al. Incompatibility between human blood and isolated islets of Langerhans: a finding with implications for clinical intraportal islet transplantation? Diabetes 1999; 48(10):1907-14.
3. Contreras J L, Eckstein C, Smyth C A, et al. Activated protein C preserves functional islet mass after intraportal transplantation: a novel link between endothelial cell activation, thrombosis, inflammation, and islet cell death. Diabetes 2004; 53(11):2804-14.
4. Amrani A, Verdaguer J, Thiessen S, Bou S, Santamaria P. IL-1alpha, IL-1beta, and IFN-gamma mark beta cells for Fasdependent destruction by diabetogenic CD4 (+) T lymphocytes. J Clin Invest 2000; 105(4):459-68.
5. Amoli M M, Bagher L. Would blockage of cytokines improve the outcome of pancreatic islet transplantation? Medical Hypotheses. 2005; 66: 816-819.
6. Flodströma M, Welsh N, and Eizirik D L. Cytokines activate the nuclear factor κB (NF-κB) and induce nitric oxide production in human pancreatic islets. FEBS Letters 1996; 385 (1-2): 4-6.
7. Grunnet L G, Aikin R, Tonnesen M F, Paraskevas S, Blaabjerg L, Størling J, Rosenberg L, Billestrup N, Maysinger D, and Mandrup-Poulsen T. Proinflammatory Cytokines Activate the Intrinsic Apoptotic Pathway in β-cells. Diabetes. 2009; 58: 1807-1815
8. Chen C, Moreno R, Samikannu B, Bretzel R G, Schumitz M L, and Linn T. Improved Intraportal Islet transplantation Outcome by Systemic IKK-beta Inhibition: NF-κB Activity in Pancreatic Islets Depends on Oxygen Availability. American Journal of Transplantation 2011; 11: 1-10.
9. Piemonti L, Leone B E, Nano R, et al. Human pancreatic islets produce and secrete MCP-1/CCL2: relevance in human islet transplantation. Diabetes. 2002; 51 (1): 55-65.

10. Mishra L C, Singh B B, Dagenais S. Scientific basis for the therapeutic use of *Withania somnifera* (ashwagandha): a review. Altern Med Rev. 2000; 5: 334-346.
11. Kaileh M, Berghe W V, Heyerick A, et al. Withaferin A Strongly Elicits IκB Kinase β Hyperphosphorylation Concomitant with Potent Inhibition of Its Kinase Activity. Journal of Biological Chemistry. 2007; 282: 4253.
12. Maitra R, Porter M A, Huang S, and Gilmour B P. Inhibition of NFκB by the natural product Withaferin A in cellular models of cystic Fibrosis inflammation. Journal of Inflammation. 2009; 6: 15.
13. Mohan R, Hammers H J, Bargagna-Mohan P, et al. Withaferina A is a potent inhibitor of angiogenesis. Angiogenesis. 2004; 7: 115-122.
14. Barnes P J. Molecules in focus Nuclear factor-κB. The International Journal of Biochemistry & Cell Biology. 1997; 29 (6): 867-870.
15. Hiscott, J., Kwon, H., and Genin, P. Involvement of FAN in TNF-induced apoptosis (2001) J. Clin. Investig. 107; 143-151.
16. Ojha S K and Arya D S. *Withania somnifera* Dunal (Ashwagandha): A promising Remedy for Cardiovascular Diseases. Wourld Journal of Medical Sciences. 2009; 4(2): 156-158.
17. Peng H, Olsen G S, Tamura Y, et al Inhibition of Inflammatory Cytokine-Induced Response in Human Islet Cells by Withaferin A. Transplantation Proceedings. 2010; 42(6): 2058-61.
18. Hawiger J. Innate immunity and inflammation: a transcriptional paradigm. Immunol Res. 2001; 23(2-3):99-109.
19. Hanada T and Yoshimura A. Regulation of cytokine signaling and inflammation. Cytokine Growth Factor Rev. 2002; 13(4-5):413-21.
20. Karin M, Delhase M. The I kappa B kinase (IKK) and NF-kappa B: key elements of proinflammatory signaling. Semin Immunol. 2000; 12(1):85-98.
21. Baeuerle, P A and Baltimore D. I kappa B: a specific inhibitor of the NF-kappa B transcription factor. 1988; 242(4878):540-6.
22. Boulton, T G and Cobb M H. Identification of multiple extracellular signal-regulated kinases (ERKs) with anti-peptide antibodies. Cell Regulation. 1991; 2(5):357-71.
23 Parry G C N and Mackman N. A Set of Inducible Genes Expressed by Activated Human Monocytic and Endothelial cells Contain κB-like Sites That Specifically Bind c-Rel-p65 Heterodimers. The Journal of Biological Chemistry. 1994; 269 (33):20823-20825.
24 Baeuerle P A and Henkel T. Function and Activation of NF-κB in the Immune System. Annual Reviews of Immunology. 1994; 12: 141-179.
25 The IκB-NF-κB Signaling Module: Temporal Control and Selective Gene Activation. Science. 2002; 298 (5596): 1241-1245.
26. Grove M, Plumb M. C/EBP, NF-kappa B, and c-Ets family members and transcriptional regulation of the cell-specific and inducible macrophage inflammatory protein alpha immediate early gene. Mol Cell Biol. 1993; 13:5276-5289.
27. Mori N, Prager D. Transactivation of the interleukin-1alpha promoter by human T-cell leukemia virus type I and type II Tax proteins. Blood. 1996; 87(8): 3410-7.
28. Huang D, Casale G P, Tian J. Quantitative Fluorescence imaging analysis for cancer biomarker discovery: application to beta-catenin in archived prostate samples. Cancer Epidemiol Biomarkers Prey. 2007; 16: 1371-1381.
29. Higher Education Commission of Pakistan (HEC), World Health Organization, International Clinical Registry Program, NCT00689195.
30. Council of Scientific & Industrial Research, New Delhi, World Health Organization Internation Clinical Registry Program, CTRI/2008/091/000053.
31. Rabinovitch A, Suarez-Pinzon W L, Shi Y, Morgan A R, Bleackley R C. DNA Fragmentation is an early event in cytokine-induced islet beta-cell destruction. Diabetologia. 1994; 37(8):733-738.
32. Sumoski W, Baquerizo H, Rabinovitch A. Oxygen free radical scavengers protect rat islet cells from damage by cytokines Diabetologia. 1989; 32 (11): 792-796.
33. Conditional and Specific Inhibition of NF-κB in Pancreatic β Cells Prevents Cytokine-Induced Deleterious Effects and Improves Islet Survival Post Transplant Rink J, Chen X, Xiaomin Z, Kaufman D B. ATC proceedings??. 2011.

What is claimed is:

1. A method of reducing number of islet cells to be transplanted, increasing a functional mass of transplanted islet cells, or both in a diabetic human subject to achieve normoglycemia comprising the steps of:
    (a) providing a dose of islet cells to be transplanted in the human subject;
    (b) transplanting the dose of the islet cells in the human subject; and
    (c) treating the islet cells with an effective amount of a Withaferin A composition disposed in a pharmaceutically acceptable carrier sufficient to reduce rejection of the transplanted islet cells.
2. The method of claim 1, wherein the Withaferin A composition is provided to the subject at one or more intervals for a fixed period of time following transplantation of the dose of the islet cells.
3. The method of claim 1, wherein the dose is a dose of islet cells sufficient to produce a normoglycemia in the diabetic subject.
4. The method of claim 1, wherein the composition reduces host inflammation against the dose of the transplanted islet cells caused by host cytokines without affecting the viability and the potency of the one or more transplanted islet cells.
5. The method of claim 1, wherein the Withaferin A composition is combined with the islet cells prior to, or during, transplantation.

* * * * *

UNITED STATES PATENT AND TRADEMARK OFFICE
CERTIFICATE OF CORRECTION

| | | |
|---|---|---|
| PATENT NO. | : 8,637,494 B2 | Page 1 of 1 |
| APPLICATION NO. | : 13/160334 | |
| DATED | : January 28, 2014 | |
| INVENTOR(S) | : Naziruddin et al. | |

It is certified that error appears in the above-identified patent and that said Letters Patent is hereby corrected as shown below:

On the Title Page, Item 75 Inventors, line 4, delete "Marlon" and insert -- Marion -- therefor.

Signed and Sealed this
Twenty-seventh Day of May, 2014

Michelle K. Lee
*Deputy Director of the United States Patent and Trademark Office*